United States Patent
Borneman et al.

(10) Patent No.: US 6,368,833 B1
(45) Date of Patent: Apr. 9, 2002

(54) ESTERASES, DNA ENCODING THEREFOR AND VECTORS AND HOST INCORPORATING SAME

(75) Inventors: William S. Borneman, San Carlos; Benjamin S. Bower, Pacifica, both of CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 08/952,445

(22) PCT Filed: Sep. 29, 1997

(86) PCT No.: PCT/US97/17614

§ 371 Date: Nov. 18, 1997

§ 102(e) Date: Nov. 18, 1997

(87) PCT Pub. No.: WO98/14594

PCT Pub. Date: Apr. 9, 1998

Related U.S. Application Data

(63) Continuation of application No. 08/722,713, filed on Sep. 30, 1996, now abandoned.

(51) Int. Cl.$^7$ .............................. C12N 9/18; C12N 15/55
(52) U.S. Cl. .................... 435/91.1; 536/23.1; 536/23.2; 435/320.1; 435/252.3; 435/325; 435/197
(58) Field of Search .............................. 536/23.1, 23.2; 435/320.1, 252.3, 325, 197, 91.1

(56) References Cited

U.S. PATENT DOCUMENTS 4,370,416 A    1/1983  Shigemichi et al. ........ 435/197

FOREIGN PATENT DOCUMENTS

| GB | 2 301 103 A | 11/1996 |
| WO | WO 97 00964 A | 9/1997 |

OTHER PUBLICATIONS

Bartolome, et al., "Influence of different xylanases on activity of ferulic acid esterase on wheat bran," *Biotechnol. Appl. Biochem.*, V. 22, pp. 65–73, 1995.

Borneman, et al., "Assay for trans–p–Coumaroyl Esterase Using a Specific Substrate from Plant Cell Walls," *Analytical Biochemistry*, V. 190, pp. 129–133 1990.

Borneman, et al., "Isolation and Characterization of p–Coumarolyl Esterase from the Anaerobic Fungus *Neocallimastix* Strain MC–2," *Applied and Environmental Microbiology*, V. 57 (8), pp. 2337–2344, Aug. 1991.

Borneman, et al., "Purification and Partial Characterization of Two Feruloyl Esterases from the Anaerobic Fungus Neocallimastix Strain MC–2," *Applied and Environmental Microbiology*, V. 58 (11), pp. 3762–3766, Nov. 1992.

Brezillon, et al., "Novel ferulic acid esterases are induced by growth of *Aspergillus niger* on sugar–beet pulp, " V. 45, pp. 371–376, 1996.

Castanares, et al., "Purification and properties of a feruloyl/p–coumaroyl esterase from the fungus *Penicillium pinophilum*," Enzyme Microb. Technbol., V. 14, pp. 875–884, Nov. 1992.

Christov, et al., "Esterases of xylan–degrading microorganisms: Production, properties, and significance," *Enzyme Microb. Technol.*, V. 15, pp. 460–475, Jun. 1993.

Dalrymple, Brian P. et al., "Expression of a Butyribibrio fibrisolvens E14 gene (cinB) encoding an enzyme with cinnamoyl ester hydrolase activity is negatively regulated by the product of an adjacent gene (cinR)", *Microbiology* (Reading), U.K.), (1997) V. 143(4), pp. 1203–1210.

Dalrymple, Brian P. et al., "Cloning of a gene encoding cinnamoyl ester hydrolase from the ruminal bacterium Butyrivibrio fibrisolvens E14 by a novel method," *FEMS Microbiol. Lett.*, (1996), V. 143 (2–3), pp. 115–120.

Donnelly, et al., "Production by Streptomyces viridosporus T7A of an Enzyme Which Cleaves Aromatic Acids from Lignocellulose," *Applied and Environmental Microbiology*, V. 54 (9), pp. 2237–2244, Sep. 1988.

Dugelay, et al., "Role of Cinnamoyl Esterase Activities from Enzyme Preparations on the Formation of Volatile Phenols during Winemaking," *J. Agric. Food Chem.*, V. 41, pp. 2092–2096, 1993.

Faulds, et al. "Release of ferulic acid from maize bran and derived oligosaccharides by Aspergillus niger esterases," *Carbohydrate Polymers*, V. 27 pp. 187–190, 1995.

Faulds, et al., "A major bioactive component of plant cell walls, ferulic acid, influences feruloyl esterase production in *Aspergillus niger*," Biochemical Society Transactions, V. 24, pp. 386S, 1996.

Faulds, et al., "Ferulic acid esterase from *Aspergillus niger*. purification and partial characterization of two forms from a commercial source of pectinase," *Biotechnol. Appl. Beochem.*, V. 17, pp. 349–359, 1993.

Faulds, et al., "Purification and characterization of a ferfulic acid esterase (FAE–III) from Aspergillus niger. specificity for the phenolic moiety and binding to microcrystalline cellulose," *Microbiology*, V. 140, pp. 779–787, 1994.

Faulds, et al., "Release of ferulic acid from plant polysaccharides by ferulic acid esterase from Streptomyces olivochromogenes," *Carbohydrate Polymers*, V. 21 pp. 153–155, 1993.

(List continued on next page.)

*Primary Examiner*—Rebecca E. Prouty
(74) *Attorney, Agent, or Firm*—Genencor International, Inc.

(57) ABSTRACT

A novel DNA is provided which encodes an enzyme having esterolytic activity isolated from Aspergillus. Also provided for is a method of isolating DNA encoding an enzyme having esterolytic activity from organisms which possess such DNA, transformation of the DNA into a suitable host organism, expression of the transformed DNA and the use of the expressed esterase protein in feed as a supplement, in textiles for the finishing of such textiles prior to sale, in starch processing or production of foods such as baked bread.

17 Claims, 12 Drawing Sheets-

OTHER PUBLICATIONS

Faulds, et al., "Release of ferulic acid from wheat bran by a ferulic acid esterase (FAE–III) from *Aspergillus niger*," *Appl. Microbiol. Biotechnol,* V. 43, pp. 1082–1087, 1995.

Faulds, et al., "Specificity of an esterase (XYLD) from *Pseudomonas fluorescens* subsp. *cellulosa,*"*Biochimica et Biophysica Acta,* V. 1243, pp. 265–269, 1995.

Faulds, et al., "The purification and characterization of 4–hydroxy–3–methoxycinnamic (ferulic) acid esterase from *Streptomyces olivochromogenes,*" *Journal of General Microbiology,* V. 137, pp. 2339–2345, 1991.

Ferreira, et al. "A modular esterase from *Pseudomonas fluorescens* subsp. *Cellulosa* contains a non–catalytic cellulose–binding domain," *Biochem. J.,* V. 294, pp. 349–355, 1993.

Hatfield, et al., "Synthesis of Methyl 5–O–trans–Feruloyl–α–L–arabinofuranoside and Its Use as a Substrate to Assess Feruloyl Esterase Activity," *Analytical Biochemistry,* V. 194, pp. 25–33, 1991.

Iiyama, et al., "Phenolic Acid Bridges between Polysaccharides and lignin in Wheat Internodes," *Phytochemistry,* V. 29 (3), pp. 733–737, 1990.

Kroon, et al., "Purification and characterization of a novel esterase induced by growth of *Aspergillus niger* on sugar––beet pulp," *Biotechnol. Appl. Biochem.,* V. 23, pp. 255–262, 1996.

Kroon, et al., "Release of ferulic acid from sugar–beet pulp by using arabinanase, arabinofuranosidase and an esterase from *Aspergillus niger,*" *Biotechnol. Appl. Biochem.,* V. 23, pp. 263–267, 1996.

MacKenzie, et al., "Ferulic Acid Esterase Activity from *Schizophyllum commune,*" *Applied and Environmental Microbiology,* V. 54 (5), pp. 1170–1173, May 1988.

McCallum, et al., "Spectrophotometric Assay and Electrophoretic Detection of trans–Feruloyl Esterase Activity," *Analytical Biochemistry,* V. 196, pp. 360–366 1991.

McCrae, et al., "Xylan–degrading enzyme system produced by the fungus *Aspergillus awamori:* isolation and characterization of a feruloyl esterase and a p–coumaroyl esterase," *Enzyme Microb. Technol.,* V. 16, pp. 826–834, Oct. 1994.

Smith, et al., "Xylan–hydrolysing enzymes from thermophilic and mesophilic fungi," *World Journal of Microbiology and Biotechnology,* V. 7, pp. 475–484, 1991.

Tenkanen, et al., "Production, purification and characterization of an esterase liberating phenolic acids from lignocellulosics," *Journal of Biotechnology,* V. 18, pp. 69–84, 1991.

Zimmermann et al., "Metal Ions In Biological Systems," Degradation Of Environmental Pollutants By Microorganisms And Their Metalloenzymes. (Ed.). V. 28, Xxxii+582p. Marcel Dekker, Inc.: New York, New York, USA; Basel, Switzerland. 1992. 357–398.

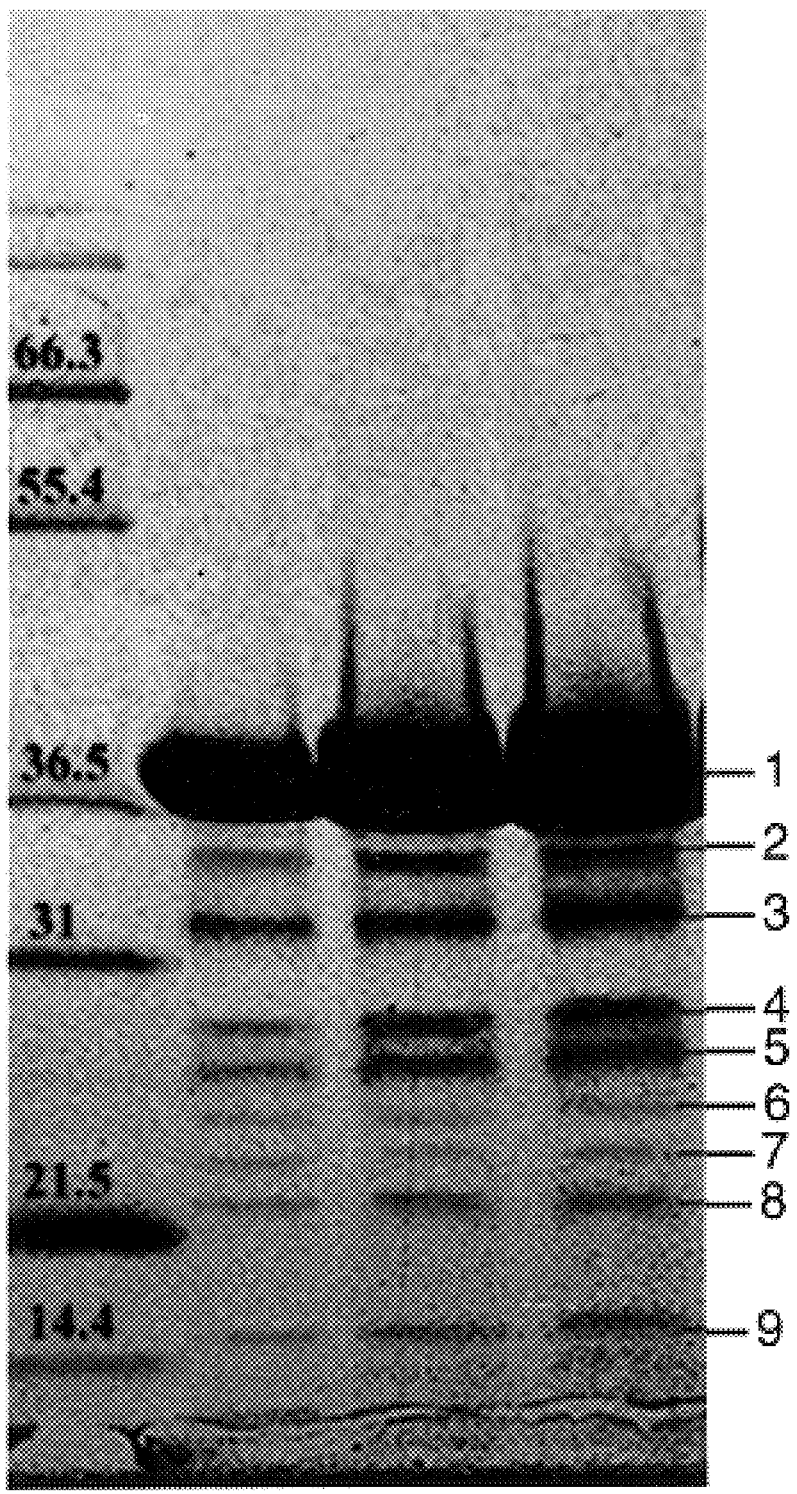
FIG._1

```
                    Bbs I                                               Msc I
GCCTCTACGCAGGGCATCTCCGAAGACCTCTACAGCCGTTTAGTCGAAATGGCCACTATCTCCCAAGTGCTGCCTACGCCGACCTGTGCAAC    90
 A  S  T  Q  G  I  S  E  D  L  Y  S  R  L  V  E  M  A  T  I  S  Q  A  A  Y  A  D  L  C  N

Sal I                                                                    Bam HI
ATTCCGTCGACTATTATCAAGGGAGAGAAAATTTACAATTCTCAAACTGACATTAACGGATCCTCCGGACGACAGCAGCAAAGAA         180
 I  P  S  T  I  I  K  G  E  K  I  Y  N  S  Q  T  D  I  N  G  W  I  L  R  D  D  S  S  K  E

Bbs I                 BsaB I
ATAATCACCGTCTTCCGTGGCACTGGTAGTGATACGAATCTACAACTCGATACTAACCCCTCACGCCTTTCGACACCCTACCACAA        270
 I  I  T  V  F  R  G  T  G  S  D  T  N  L  Q  L  D  T  N  Y  T  L  T  P  F  D  T  L  P  Q

Bsa I      Tth111 I    BspM I
TGCAACGGTTGTGAAGTACACGGTGGATATATTATTGGATGGGTCTCCGTCCAGGACCAAGTCGAGTCGCTTGTCAAACAGCAGGTTAGC    360
 C  N  G  C  E  V  H  G  G  Y  Y  Y  I  G  W  V  S  V  Q  D  Q  V  E  S  L  V  K  Q  Q  V  S

Bsi I
CAGTATCCGGACTATGCGCTGACTGTGACGGGCCACAGGTATGCCCTCGTGATTTCTTTCAATTAAGTGTATAATACTCACTAACTCTAC    450
 Q  Y  P  D  Y  A  L  T  V  T  G  H  S
                                      └──────────── putative 57 bp intron ────────────┘
```

FIG._2A

GATAGTCTCGGAGCGTCCCTGGCAGCACTCACTGCCGCCCAGCTGTCTGCCACATACGACAACATCCGCCTGTACACCTTCGGCGAACCG

L G A S L A A L T A A Q L S A T Y D N I R L Y T F G E P

ApaBI  PvuII  BsrGI

CGCAGCGGGCAATCAGGCCTTCGCGTCGTACATGAACGATGCCTTCCAAGCCTCGAGCCCAGATACGACGCAGTATTTCCGGGTCACTCAT

R S G N Q A F A S Y M N D A F Q A S S P D T T Q Y F R V T H

StuI  XhoI

GCCAACGACGGGCATCCCCAAA

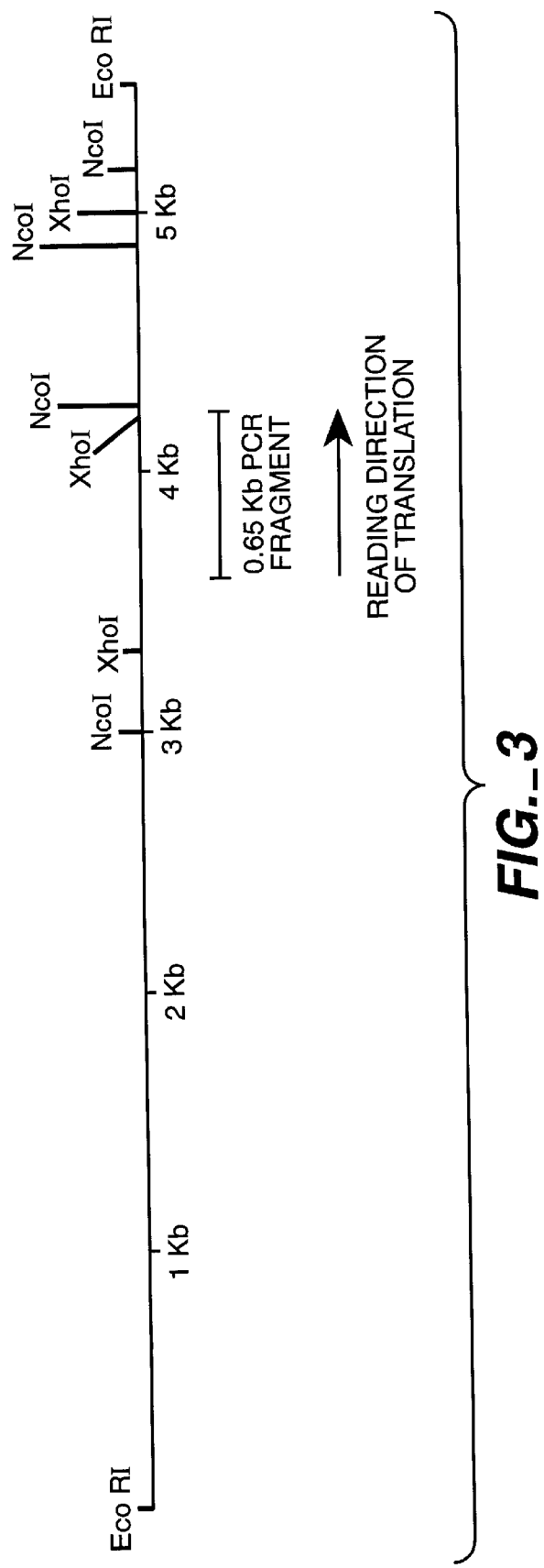

```
Nco I    EcoR V                    Psp1406 I
CCATGGTGGTGTCGATATCGGCAGTAGTCTTTGCCGAAACGTTGAGGGTTACAGTGATCTGCCGTCGGACATACTTCGGGGAATCTACGGC
                                                                                          90

Sac I
GGAATATCAAAGTCTTCGGAATATCCATATTGGGAAAGGACAGAAGTCTCCGGGGTAGTTTGATAGATGAGCTCCGGTGTATTAAATCGGG
                                                                                         180

BssH II
AGCTGACAGGAGTGAGCGTCATGTAGACCACCATCTAGTAATGTCAGTCGCGCCAATTTCGCACATGAAACAAGTTGATTTCGGGACCCCAT
                                                                                         270

Xho I              Bst1107 I                                      EclHK I
TGTTACATCTCTCGGCTACAGCTCGAGATGTGCCTGCCGAGTATACTTAGAAGCCATGCCAGCGTGTTGTTATACGACCAAAGTCAGGG
                                                                                         360

Pvu I
AATATGAAACGATCGTCGGATATTTCTGTTTTATCCTAAATTAGTCTTCCCAGTGGTTTATTTAAGAGATAGATCCCTTCACAAACACT
                                                                                         450

Xmn I
CATCCAACGGACTTCTCTCATACCACTCATTGACATAATTTCAAACAGCTCCAGGCGCATTTAGTTCAACATGAAGCAATTCTCCGCCAAAC
                                                                                         540

┌─────────────────┐
                                                           │ signal sequence │
                                                           └─────────────────┘
                                                              M  K  Q  F  S  A  K
```

*FIG._4A*

```
                Pst I    Bpu10 I
ACGTCCTCGCAGTTGTGGTGACTGCAGGGCACGCCTTAGCAGCCTCTACGCAAGGCATCTCCGAAGACCTCTACAGCCGTTTAGTCGAAA   630
           ┌─────────────────┐
           │ signal sequence │
           └─────────────────┘
 H  V  L  A  V  V  V  T  A  G  H  A  L  A  A  S  T  Q  G  I  S  E  D  L  Y  S  R  L  V  E
  Msc I                                           Sal I
TGGCCACTATCTCCCAAGCTGCCTACGCCGACCTGTGCAACATTCCGTCGACTATTATCAAGGGAGAGAAAATTTACAATTCTCAAACTG   720
 M  A  T  I  S  Q  A  A  Y  A  D  L  C  N  I  P  S  T  I  I  K  G  E  K  I  Y  N  S  Q  T
            BamH I                                                         BsaB I
ACATTAACGGATGGATCCTCCGCGACGACAGCAGCAAAGAAATAATCACCGTCTTCCGTGGCACTGGTAGTGATACGAATCTACAACTCG   810
 D  I  N  G  W  I  L  R  D  D  S  S  K  E  I  I  T  V  F  R  G  T  G  S  D  T  N  L  Q  L
                                                                               Eco31 I
ATACTAACTACACCCTTCACGCCTTTGACACCCTTACCACACAATGCAACGGTTGTGAAGTACACGGTGGATATTATTGGATGGGTCTCCG   900
 D  T  N  Y  T  L  T  P  F  D  T  L  P  Q  C  N  G  C  E  V  H  G  G  Y  Y  I  G  W  V  S
```

*FIG._4B*

```
                                    BspM I                                                Acc III
        Tth111 I         ......                                                           ......
        ......
        TCCAGGACCAAGTCGAGTCGCTTGTCAAACAGCAGGTTAGCCAGTATCCGGACTGTGACGGGCCACAGGTATGCCCTCG        990

V  Q  D  Q  V  E  S  L  V  K  Q  Q  V  S  Q  Y  P  D  Y  A  L  T  V  T  G  H    ┌─────┐
                                                                                           │intron│
                                                                             ApaB I  Pvu II│     │
                                                                             ......  ......│     │
        TGATTTCTTTCAATTAAGTGTATAATACTCACTAACTCTACGATAGTCTCGGAGGCGTCCCTGGCAGCACTCGCCGCCCAGCTGTCTG 1080

S
                                                    ┌────┐  L  G  A  S  L  A  A  L  T  A  A  Q  L
                                                    │intron│                  Stu I
                                                    │    │                    ......
              BsrG I                                │    │
              ......                                │    │
        CGACATACGACAACATCCGCCTGTACACCTTCGGCGAACTCAGGCCTCGCTCGTACATGAACGATGCCTTCCAAG               1170

A  T  Y  D  N  I  R  L  Y  T  F  G  E  P  R  S  G  N  Q  A  F  A  S  Y  M  N  D  A  F  Q

Xho I                                                                    BspM I    Nco I
        ......                                                                   ......    ......
        CCTCGAGCCCAGATACGACGACAGTATTTCCGGGTCACTCATGCCAACGACGGCATCCCCAAACCTGCCCCCGGTGGAGCAGGGTACGCCC 1260

A  S  S  P  D  T  T  Q  Y  F  R  V  T  H  A  N  D  G  I  P  N  L  P  P  V  E  Q  G  Y  A

Sca I
              ......
        ATGGCGGGTGTAGAGTACTGGAGCGTTGATCCTTACAGCGCCCAGAACACATTTGTCTGCACTGGGGATGAAGTGCAGTGCTGTGAGGCCC 1350

```
                                Fsp I                                    BsrB I      BsrG I      Bcl I
AGGGCGGACAGGGTGTGAATAATGCGCACACGACTTATTTTGGGATGACGAGGGAGCCTGTACATGGTGATCAGTCATTTCAGCCTCCC       1440
 Q  G  G  Q  G  V  N  N  A  H  T  T  Y  F  G  M  T  S  G  A  C  T  W  .

Ppu10 I
                                         BfrB I   SnaB I                                     BspLU11 I
                                         Sph I    Bst1107 I
CGAGTGTACCAGGAAAGATGTCCTGGAGAGGGCATGCATGTACGTATACCCGAAGCACACTTTTTCGGTAAATCAGGACACATGTAAT       1530

BstE II                                                                          Dra I
AAGTTCCTTCCATGAATAGATATGGTTACCCTCACCATAAGCCTTGAGGTTGCCTTTCTCTTTTGATTGTGAATATATATTTAAAGTAGA     1620

EcoR V
TGACAGATATCTCTAAACACCTTATCCGCTTAAACCCATCATAGATTGTGTCACGTGATAGAGCCCCTTGAATGATGAGCGAAATGTATCA   1710

Dra I                                                                           Sca I                Ppu10 I
GTCCCGTTTAAAATCAAACCCTTTCAGCCTTCAGCCTTCAGCCTAGCACAGTCAGATAATACACCAACCCCATTCTAAGGTAGTACTAAATATGAATACAGCCTAAA  1800

Bgl II                                  Ear I       Nhe I   Nco I      Eco31 I
                                                                                  Sap I
 BfrB I
TGCATCGCTATATGATCCCATAAAGAAGCAACAACCTTTCAGATCTCGTTTGCCTGCGAAGAGCTAGCTCTACCATGGTCTCAATTAT      1890

FIG._4D
```

```
                                                                                              BamH I
                                                                                              Xma I
                                                     BspLU11 I                                Sma I
                                                     BsrG I
GAGTGGGAGCGTTTAGTCTCGTTTAAGCCTAGCTATCTTATAAGGACAACACATGTACATGGGCCTTACTTGTAGAGAGGTAGGATCCCGGG 1980

Xho I            BseR I                             Tth111 I
CTTCTTCACATCTCGAGGAGTTGTCTACACGTCGCGTCCATGTCATAAGCCGGTACTCGACGTTGTCGTGACCGTGACCCAGACCCCTGT 2070

Nco I                     BsaB I
TGATAGCCGTTGAGAAGGCCCTATATTTGAATTTCCAATCTCAGCTTTACGAAGATATGCCCATGGTGGAGGGTTAGTAAACCGATGATGA 2160

Eco31 I    Msc I                                               BspLU11 I
TCGTGTGCAGCATGAGAGATGAGACCGTGGCCAATCCTGTTCAAATGCCAAGACCCGCCTCTACCACACATGTAAGGCATCCGTCGGCCAC 2250
                                        Xcm I                            Msc I               BsrD I
GTTGAATTGTGCAAATGCCGAGATCATAAAAGCGGCACACTTCCACGTGGTACTGATGGGTTGCCGCCGTGGCCATACTGTGTTTTCCA 2340

Alwn I                       Ear I              Vsp I
TTGCGTGGGTCGTTCGTGTTACTGCGACGCAGGGCTCTCTTCTGAGGTAGAAAACACCCCATATTAATCT 2430

EcoR I
GAATTC → 2436
```

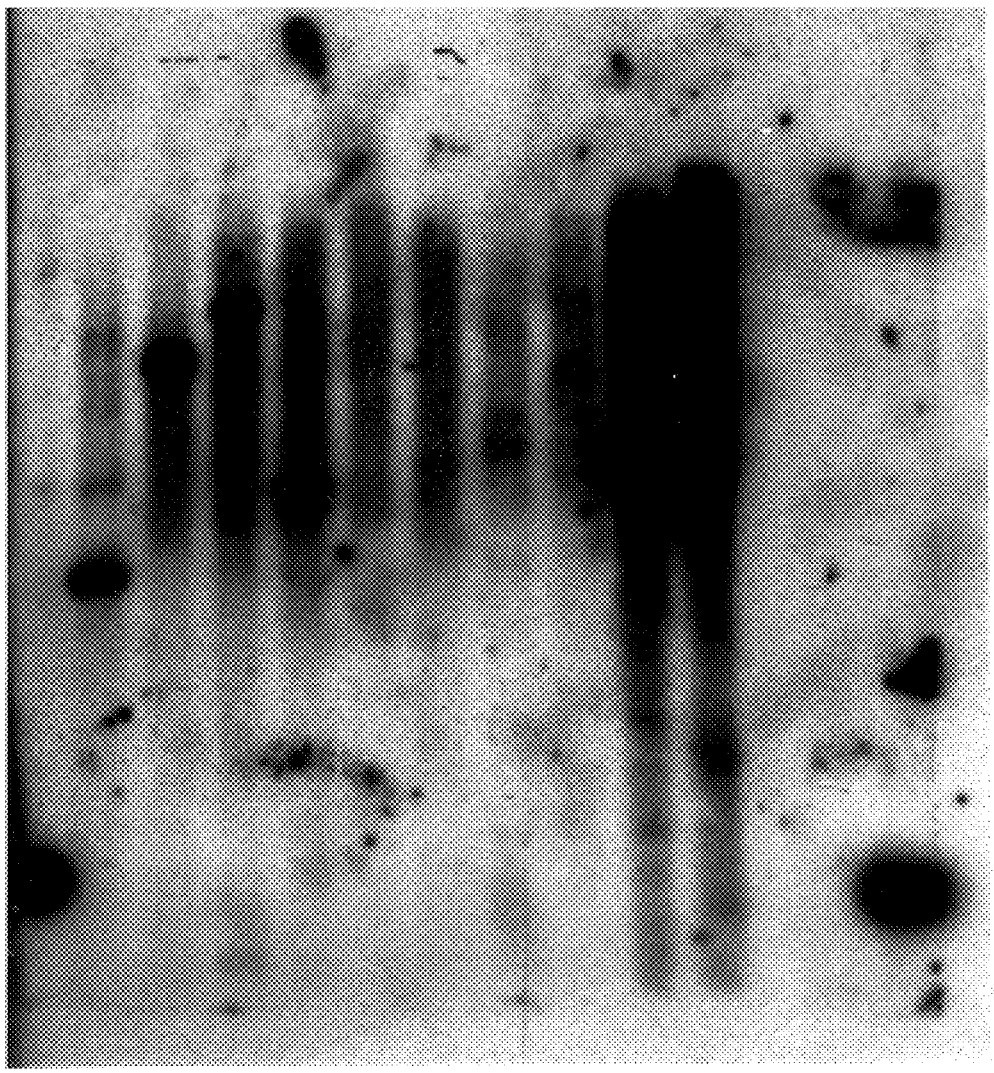
FIG._6

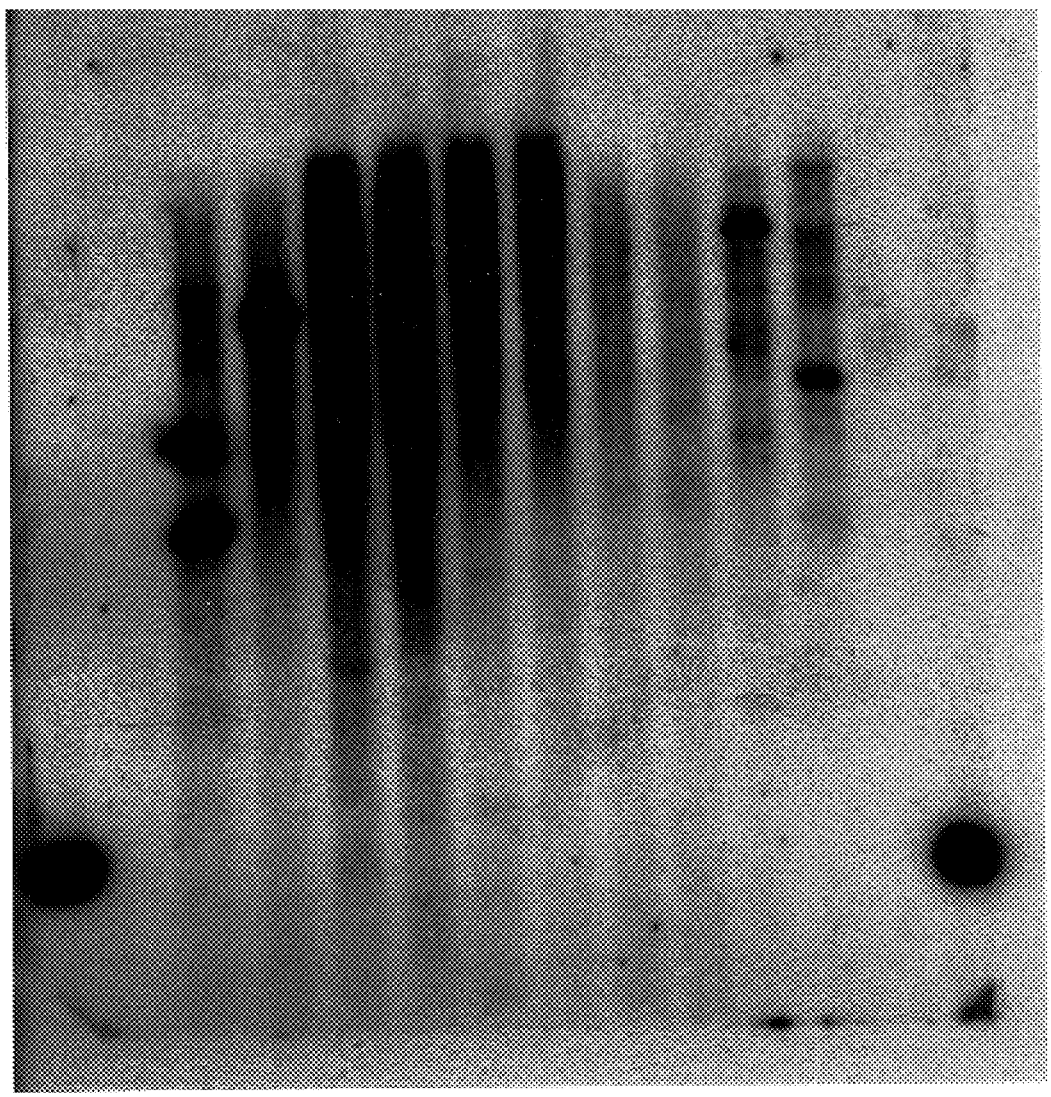
FIG._7

US 6,368,833 B1

ESTERASES, DNA ENCODING THEREFOR AND VECTORS AND HOST INCORPORATING SAME

This application is a continuation of application Ser. No. 08/722,713 filed Sep. 30, 1996, now abandoned.

BACKGROUND OF THE INVENTION

The present invention is directed to a novel esterolytic enzyme, novel genetic material encoding that enzyme and esterolytic proteins developed therefrom. In particular, the present invention provides an esterase derived from Aspergillus, a DNA encoding that esterase, vectors comprising that DNA, host cells transformed with that DNA and a protein product produced by such host cells.

Xylan, next to cellulose, is the most abundant renewable polysaccharide in nature. It is the major hemicellulosic component in plants and is located predominantly in the secondary cell walls of angiosperms and gymnosperms. The composition and structure of xylan are more complicated than that of cellulose and can vary quantitatively and qualitatively in various woody plant species, grasses, and cereals. Xylan is a heteropolymer in which the constituents are linked together not only by glycosidic linkages but also by ester linkages. Ferulic acid is the most abundant hydroxycinnamic acid found in plants and is known to be esterified to arabinose in wheat bran, wheat flour, barley straw, maize, sugar-cane bagasse, rice straw and other monocotyledons and also found esterified to galactose residues in pectins of sugar beet, spinach and other dicotyledons. p-Coumaric acid is also linked in a similar fashion in monocots. The presence of these phenolic acids has been shown to limit cell-wall biodegradation and play significant roles in cell wall extension and stabilization through cross-linking heteroxylan chains by forming phenolic dimers via plant peroxidases and/or photodimerization initiated by sunlight. Further, phenolic acids have been shown to function as cross-links between cell wall polysaccharides and the phenylpropanoid lignin polymer. The covalent attachment of lignin to wall polysaccharides and the crosslinking of xylan chains within hemicellulose limit overall polysaccharide bioavailability resulting in significant amounts of undigested fiber in animal feedstuffs, poor bioconversion of agricultural residue into useful products and incomplete processing of grains.

Enzyme hydrolysis of xylan to its monomers requires the participation of several enzymes with different functions. These are classified in two groups based on the nature of the linkages that they cleave. The first group of enzymes is hydrolases (EC 3.2.1) involved in the hydrolysis of the glycosidic bonds of xylan. These include endo-xylanases (EC 3.2.1.8) which randomly dismember the xylan backbone into shorter xylooligosaccharides; β-xylosidase (EC 3.2.1.37) which cleave the xylooligosaccharides in an exo-manner producing xylose; α-L-arabinofuranosidase (EC 3.2.1.55); and α-glucoronidase (EC 3.2.1.1) which remove the arabinose and 4-O-methylglucuronic acid substituents, respectively, from the xylan backbone. The second group includes enzymes that hydrolyze the ester linkages (esterase, EC 3.1.1) between xylose units of the xylan polymer and acetyl groups (acetyl xylan esterase, EC 3.1.1.6) or between arabinosyl groups and phenolic moieties such as ferulic acid (feruloyl esterase) and p-coumaric acid (coumaroyl esterase).

Faulds et al., reported two forms of ferulic acid esterase isolated from Aspergillus niger. The different esterases were distinguished on the basis of molecular weight and substrate specificity (Faulds et al., Biotech. Appl. Biochem., vol. 17, pp. 349–359 (1993)). Brezillon et al. disclosed the existence of at least two cinnamoyl esterases which were believed to be distinct from the ferulic acid esterases shown in the prior art (Brezillon et al., Appl. Microb. Biotechnol., vol. 45, pp. 371–376 (1996)). A ferulic acid esterase called FAE-III was isolated from Aspergillus niger CBS 120.49 and shown to act together with xylanase to eliminate nearly all of the ferulic acid and low molecular mass xylooligosaccharides in a wheat bran preparation; ferulic acid was also removed without the addition of xylanase, albeit at a lower level. Faulds et al. further isolated and partially characterized FAE-III from Aspergillus niger CBS 120.49 grown on oat spelt xylan (Faulds et al., Microbiology, vol. 140, pp. 779–787 (1994)) and showed it to have a pI of 3.3, a molecular weight of 36 kD (SDS-PAGE) and 14.5 kD (Gel Filtration method), a pH optimum of 5 and a temperature optimum of 55–60° C.; microcrystalline cellulose binding was also detected. The authors theorized that FAE-II may be a proteolytically modified FAE-III. Recently, the various known ferulic acid esterases derived from Aspergillus niger have been distinguished based on their distinct substrate specificity and it was noted that FAE-II and FAE-III were unable to release ferulic acid from sugar beet pulp (Brezillon et al., supra).

Nonetheless, despite the characterization work which has been directed to Aspergillus niger esterases, the art remains in need of additional esterases for its various applications. Further, those of skill in the art have thus far failed to discover a nucleotide sequence which can be used to produce more efficient genetically engineered organisms capable of expressing such esterases in large quantities suitable for industrial production. However, a pressing need exists for the development of an esterase expression system via genetic engineering which will enable the purification and utilization of working quantities of relatively pure enzyme.

SUMMARY OF THE INVENTION

It is an object of the present invention to provide for novel esterase proteins and DNA encoding such proteins.

It is an object of the present invention to provide for a method of isolating DNA from many different species, which DNA encodes protein having esterase activity.

It is a further object of the present invention to provide for an esterase which is produced by a suitable host cell which has been transformed by the DNA encoding the esterolytic activity.

The present invention provides for a purified 38 kD esterase which is derived from Aspergillus niger. Further, a DNA sequence coding for the 38 kD esterase comprising a DNA as shown in FIG. 4 (SEQ. ID NO: 27); a DNA which encodes the amino acid sequence also shown in FIG. 4 (SEQ. ID NO: 28); a DNA which encodes an esterase which comprises an amino acid segment which differs from the sequence in FIG. 4, provided that the DNA encodes a derivative of the 38 kD esterase specifically described herein; and a DNA which encodes an esterase that comprises an amino acid segment which differs from the sequence in FIG. 4, provided that the DNA hybridizes under low-stringency conditions and/or standard stringency conditions, as defined below, with a DNA comprising all or part of the DNA in FIG. 4 are provided. The present invention further encompasses vectors which include the DNA sequences described above, host cells which have been transformed with such DNA or vectors, fermentation broths comprising such host cells and esterase proteins encoded by such DNA which are expressed by the host cells. Preferably, the DNA of the invention is in substantially purified form and is used to prepare a transformed host cell capable of producing the encoded protein product thereof. Additionally, polypeptides which are the expression product of the DNA sequences described above are within the scope of the present invention.

The enzyme of the instant invention has application as a supplement to an animal feed; in a process for treating fabric; to improve the mechanical properties of dough and the end product of baking of foods; in the modification of polysaccharides to give novel properties, e.g., gums; and in the processing grains. Further, the enzyme also has application in processing of plant materials for the release of free phenolic groups for use as an antioxidant, photoprotector, anti-inflammatory and/or anti-microbial agent which find use in personal care products such as cosmetics and as an aid in the conversion of chemical feed stocks to valuable specialty chemicals, food additives and flavorings.

An advantage of the present invention is that a DNA has been isolated which provides the capability of isolating further DNAs which encode proteins having esterolytic activity.

Another advantage of the present invention is that, by virtue of providing a DNA encoding a protein having esterolytic activity, it is possible to produce through recombinant means a host cell which is capable of producing the protein having esterolytic activity in relatively large quantities.

Yet another advantage of the present invention is that commercial application of proteins having esterolytic activity is made practical.

BRIEF DESCRIPTION OF THE DRAWINGS

FIG. 1 illustrates a western blot following SDS-PAGE gel showing the fragmentation of FAE under denaturing conditions.

FIG. 2 illustrates the DNA sequence (SEQ. ID NO: 25) with deduced introns and amino acid sequence (SEQ. ID NO: 26) of a 650 base pair fragment corresponding to the gene encoding a 38 kD esterase isolated from *Aspergillus niger*.

FIG. 3 illustrates a restriction map of a DNA fragment containing the gene encoding the 38 kd esterase.

FIGS. 4A–4E illustrate the complete DNA (SEQ. ID NO: 27), with highlighting to point out the signal sequence, intron and various restriction endonuclease sites, and amino acid sequence (SEQ. ID NO: 28) corresponding to the gene encoding the 38 kD esterase isolated from *Aspergillus niger*.

FIG. 5 illustrates the DNA sequence of the gene encoding the 38 kD esterase (SEQ. ID. NO: 29).

FIG. 6 illustrates a southern blot gel showing hybridization between a DNA probe derived from the 38 kD esterase of the invention and several other filamentous fungi ("gel 1").

FIG. 7 illustrates a southern blot gel showing hybridization between a DNA probe derived from the 38 kD esterase of the invention and several other filamentous fungi ("gel 2").

DETAILED DESCRIPTION OF THE INVENTION

"Esterase" or "esterolytic activity" means a protein or peptide which exhibits esterolytic activity, for example, those enzymes having catalytic activity as defined in enzyme classification EC 3.1.1. Esterolytic activity may be shown by the ability of an enzyme or peptide to cleave ester linkages, for example, feruloyl, coumaroyl or acetyl xylan groups, from organic compounds in which they are known to exist, e.g., primary and secondary cell walls. Preferably, the esterase comprises an esterolytic activity which cleaves the ester linkage of phenolic esters such as: [5O-((E)-feruloyl)-α-L-arabinofuranosyl](1→3)-O-β-D-xylopyranosyl-(1→4)-D-xylopyranose (also known as FAXX); [5-O-((E)-feruloyl)-α-L-arabinofuranosyl](1→3)-O-β-D-xylopyranose (also known as FAX); O-β-D-xylopyranosyl-(1→4)-O-[5-O-((E)-feruloyl)-α-arabinofuranosyl-(1→3)]-O-β-D-xylopyranosyl-(1→4)-D-xylopyranose (also known as FAXXX); [5-O-((E)-p-coumaroyl)-α-L-arabinofuranosyl](1→3)-O-β-D-xylopyranosyl-(1→4)-D-xylopyranose (also known as PAXX); [5-O-((E)-p-coumaroyl)-α-L-arabinofuranosyl](1→3)-O-β-D-xylopyranose (also known as PAX); O-β-D-xylopyranosyl-(1→4)-O-[5-O-((E)-p-coumaroyl)-α-arabinofuranosyl-(1→3)]-O-β-D-xylopyranosyl-(1→4)-D-xylopyranose (also known as PAXXX) and other ester linked phenolic oligosaccharides as are known in the art. Such esterases are generally referred to as ferulic acid esterase (FAE) or enzymes having feruloyl esterase activity. It has surprisingly been discovered that an esterase having ferulic acid esterase activity which may be purified from *Aspergillus niger*, as described herein, and having an amino acid sequence as shown in FIG. 4, further has activity on sugar beet pulp and also proteolytic and lipolytic activity. Thus, according to a particularly preferred embodiment of the present invention, an esterase and/or a DNA encoding that esterase is provided which esterase also has lipolytic and/or proteolytic activity. Accordingly, the esterase of the invention having measurably significant esterolytic activity on feruloyl and coumaroyl esters also has proteolytic and lipolytic activity.

Preferably, the esterase and/or DNA encoding the esterase according to the present invention is derived from a fungus, more preferably from an anaerobic fungus and most preferably from Aspergillus spp., e.g., *Aspergillus niger*. Thus, it is contemplated that the esterase or the DNA encoding the esterase according to the invention may be derived from Absidia spp.; Acremonium spp.; Actinomycetes spp.; Agaricus spp.; Anaeromyces spp.; Aspergillus spp., including *A. auculeatus, A. awamori, A. flavus, A. foetidus, A. fumancus, A. fumigatus, A. nidulans, A. niger, A. oryzae, A. terreus* and *A. versicolor*; Aeurobasidium spp.; Cephalosporum spp.; Chaetomium spp.; Coprinus spp.; Dactyllum spp.; Fusarium spp., including *F. conglomerans, F. decemcellulare, F. javanicum, F. lini, F.oxysporum* and *F. solani*; Gliocladium spp.; Humicola spp., including *H. insolens* and *H. lanuginosa*; Mucor spp.; Neurospora spp., including *N. crassa* and *N. sitophila*; Neocallimastix spp.; Orpinomyces spp.; Penicillium spp; Phanerochaete spp.; Phlebia spp.; Piromyces spp.; Pseudomonas spp.; Rhizopus spp.; Schizophyllum spp.; Streptomyces spp; Trametes spp.; and Trichoderma spp., including *T. reesei, T. longibrachiatum* and *T. viride*; and Zygorhynchus spp. Similarly, it is envisioned that an esterase and/or DNA encoding an esterase as described herein may be found in bacteria such as Streptomyces spp., including *S. olivochromogenes*; specifically fiber degrading ruminal bacteria such as *Fibrobacter succinogenes*; and in yeast including *Candida torresii, C. parapsilosis; C. sake; C. zeylanoides; Pichia minuta; Rhodotorula glutinis; R. mucilaginosa*; and *Sporobolomyces holsaticus*.

According to a preferred embodiment of the invention, the esterase is in a purified form, i.e., present in a particular composition in a higher or lower concentration than exists in a naturally occurring or wild type organism or in combination with components not normally present upon expression from a naturally occurring or wild type organism.

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control such transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter and a preferred promoter used in *Aspergillus niger* is glaA. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4,phage DNAs e.g., the numerous derivatives of phage λ, e.g., NM989, and other DNA phages, e.g., M13 and filamentous single stranded DNA phages, yeast plasmids such as the 2 μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., Molecular Cloning: A Laboratory Manual, Second Edition, Cold Spring Harbor Press (1989). Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70–76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichoderma longibrachiatum, Saccharomyces cerevisiae* or *Aspergillus niger*, and preferably *Aspergillus niger*. Host cells are transformed or transfected with vectors constructed using recombinant DNA techniques. Such transformed host cells are capable of both replicating vectors encoding esterase and its variants (mutants) or expressing the desired peptide product.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme), which peptides retain a characteristic enzyme nature of the precursor enzyme but which have altered properties in some specific aspect. A "derivative" within the scope of this definition will retain generally the characteristic esterolytic activity observed in the native or parent form to the extent that the derivative is useful for similar purposes as the native or parent form, However, it is further contemplated that such derivatives may have altered substrate specificity, e.g., greater or lesser affinity for a specific substrate such as feruloyl, cinnamoyl or coumaroyl groups, or modified pH, temperature or oxidative stability. The derivative of the invention may further be produced through chemical modification of the precursor enzyme to alter the properties thereof.

Hybridization is used herein to analyze whether a given fragment or gene corresponds to the esterase described herein and thus falls within the scope of the present invention. The hybridization assay is essentially as follows: Genomic DNA from a particular target source is fragmented by digestion with a restriction enzyme(s), e.g., EcoR I, Hind III, PinA I, Mlu I, Spe I, Bgl II, Ppu10 I, Mfe I, Nco I, Bln I, Eag I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution for 30 minutes (such as, for example, 0.25M HCl) with gentle shaking followed by denaturation for 30 minutes (in, for example, 0.4 M NaOH) with gentle shaking. The DNA should then be transferred onto an appropriate positively charged membrane, for example the Maximum Strength Nytran Plus membrane (Schleicher & Schuell, Keene, N.H.), using a transfer solution (such as, for example, 0.4 M NaOH). After the transfer is complete, generally at about 2 hours or greater, the membrane is rinsed and air dried at room temperature after using a rinse solution (such as, for example, 2×SSC[2×SSC=300 mM NaCl, 30 mM trisodium citrate]). The membrane should then be prehybridized (for approximately 2 hours or more) in a suitable prehybridization solution (such as, for example, an aqueous solution containing per 100 mls: 20–50 mls formamide, 25 mls of 20×SSPE (1×SSPE=0.18 M NaCl, 1 mM EDTA, 10 mM $NaH_2PO_4$, pH 7.7), 2.5 mls of 20% SDS, 1 ml of 10 mg/ml sheared herring sperm DNA and 21.5 ml distilled $H_2O$). As would be known to one of skill in the art, the amount of formamide in the prehybridization solution may be varied depending on the nature of the reaction obtained according to routine methods. Thus, a lower amount of formamide may result in a more complete gel in terms of identifying hybridizing molecules than the same procedure using a larger amount of formamide. On the other hand, a strong hybridization band may be more easily visually identified by using more formamide.

The DNA probe derived from the sequence in FIGS. 4 or 5 should be isolated by electrophoresis in 1% agarose, the fragment excised from the gel and recovered from the excised agarose. This purified fragment of DNA is then random prime $^{32}$P labeled (using, for example, the Megaprime labeling system according to the instructions of the manufacturer (Amersham International plc, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, for 18 hours at 37° C. with gentle shaking. The membrane is rinsed (for example, in 2×SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will depend on the washing conditions to which the filter from the Southern Blot is subjected after hybridization. "Low-stringency" conditions as defined herein will comprise washing a filter from a Southern Blot with a solution of 0.2×SSC/0.1% SDS at 20° C. for 15 minutes. "Standard-stringency" conditions comprise a further washing step comprising washing the filter from the Southern Blot a second time with a solution of 0.2×SSC/0.1% SDS at 37° C. for 30 minutes.

FIGS. 4 and 5 illustrates the amino acid sequence and DNA sequence of a novel esterase derived from *Aspergillus niger*. The isolated esterase has a molecular weight of about 38 kD (as shown on SDS-PAGE), a pI of about 2.8 (as shown on IEF), a pH optimum of about 5.1 on methyl ferulate, a temperature optimum of about 55° C. and activity on coumaroyl and feruloyl esters, and sugar beet pulp. The FAE gene shown in FIG. 4 (SEQ. ID NO: 27) is approximately 2436 base pairs in length including deduced intron sequence and, if expressed, will encode the herein identified esterase from *Aspergillus niger* (hereinafter the "38 kD esterase"). For the purposes of the present invention, the term "38 kD esterase" means an esterase derived from *Aspergillus niger* corresponding to the esterase specifically exemplified herein. The DNA provided in FIGS. 4 or 5 will be useful for obtaining homologous fragments of DNA from other species, and particularly from anaerobic fungi, which encodes an enzyme having esterolytic activity.

The DNA sequences of the present invention may be expressed by operatively linking them to an expression control sequence in an appropriate expression vector and employed in that expression vector to transform an appropriate microbial host according to techniques well established in the art. The polypeptides produced on expression of the DNA sequences of this invention may be isolated from the fermentation of animal cell cultures and purified in a variety of ways according to well established techniques in the art. One of skill in the art is capable of selecting the most appropriate isolation and purification techniques.

The esterase isolated according to the present invention is useful in applications in which it is desired to remove phenolic constituents of xylan oligosaccharides. For example, esterases may be applied to improve animal, and possibly human, nutrition as the digestibility of forage cell walls appears to be dependent on the phenolic content of the forage. Furthermore, esterases could be applied in the pulp and paper industry as hydrolysis of phenolic ester linked moieties from lignin may contribute to solubilization of s the lignin and also may contribute to hydrolysing lignin/ hemicellulose linkages. Esterases may be of potential use in the synthesis of carbohydrate derivatives and in the bioconversion of agricultural residue to fermentable sugars and free phenolic acid useful as an antioxidant, photoprotectant and/ or antimicrobial in foods and personal care products; as a feed stock for conversion to flavors (such as vanillin) biopolymers, and valuable chemicals. Esterases have also been implicated in the finishing of textile fibers (see e.g., PCT Publication No. 96/16136). The activity of esterases toward multiple substrates present in many dirt based stains, their activation by surfactants and specificity toward phenolics suggests that esterases may also be of value in detergents. The availability of relatively large quantities of esterase facilitated by the present invention will enable the development of additional valuable applications.

The invention will be explained further below in the accompanying examples which are provided for illustrative purposes and should not be considered as limitative of the invention.

EXAMPLES

Example 1

Purification and Isolation of Peptides Comprising Ferulic Acid Esterase Activity and Design of Degenerate DNA Fragments for PCR A fermentation broth from *Aspergillus niger* was filtered (0.8 μm) and 10 ml transferred into a centrifuge tube (50 ml) at room temperature. Saturated $(NH_4)_2SO_4$ was added to give a final concentration of 60%. The solution was mixed and stored for approximately one hour at 4° C. then centrifuged at 1500×g for 20 minutes at 4° C. The supernatant was removed and the pellet resuspended in distilled water. Four tubes prepared as above were combined and diluted to approximately 200 ml with ammonium sulfate (2 M) to give a final concentration of 1.2 M ammonium sulfate, the pH was adjusted to pH 7.4 by the addition of Tris-HCl (200 mM).

The enzyme sample was chromatographed by hydrophobic interaction chromatography (Poros® HPEM phenyl ether, Perseptive BioSystems, perfusion chromatography, 12×30 cm). The column was connected to a BioCad® Perfusion Chromatography Workstation (Perseptive BioSystems) and equilibrated with 5 column volumes Tris-HCl (50 mM, pH 7.4) plus 1.2 M ammonium sulfate. The sample (205 ml) was applied to the column and separated at a flow rate of 30 ml/min with a linear gradient from 1.2 M to 200 mM ammonium sulfate over 20 column volumes. Fractions (15 ml) were collected during the gradient phase of the separation and assayed for FAE activity with methyl ferulate by the method of Faulds and Williamson (1994, Microbiology 140: 779–787). Four fractions eluting at 750 mM ammonium sulfate contained 83% of the starting FAE activity. Active fractions were pooled (60 ml), dialysed by ultrafiltration into start buffer for next chromatographic step (10 kDa membrane, 20 L of 25 mM sodium acetate buffer pH 5.0). The sample was concentrated to 10 ml in preparation for ion exchange chromatography.

Ion exchange chromatography was performed using a MonoQ strong anion exchanger (MonoQ®, HR 10/10, Pharmacia Biotechnology) connected to BioCAD Perfusion Chromatography Workstation and equilibrated with 25mM sodium acetate (pH 5.0). The sample (10 ml) was applied to the column and eluted at a flow rate of 5 ml/min with a linear NaCl gradient (0–500 mM) over 15 column volumes. Fractions (5 ml) were collected during the gradient and assayed for FAE activity (activity against feruloyl esters). FAE activity eluted as a single peak at 155 mM NaCl and was collected in one fraction. The sample was concentrated (Centricon, 10 kDa) to 1.5 ml.

High performance size exclusion chromatography (HPSEC) was carried out using two Superdex 75 columns (10/30 HR, Pharmacia Biotechnology) connected in tandem on a BioCAD Perfusion Chromatography Workstation. The columns were equilibrated with 10 column volumes sodium acetate buffer (25 mM, pH 5.0) containing 125 mM NaCl and 0.01% triton X-100. The columns were calibrated for determination using protein standards of known molecular mass (Bio-RAD gel filtration standards, and Sigma gel filtration. standards). Samples (500 µl) were applied and separated at a flow rate of 750 µl/min. Fraction (1 ml) were collected. The FAE activity eluted as a single peak corresponding to a molecular mass of about 32 kDa.

Upon native PAGE of a desalted active fraction from HPSEC a single protein band was observed. The isoelectric point of the FAE was determined using Phast gel Dry IEF equilibrated with a solution ampholyte, (20% final concentration, containing a mix of pI 2-4, 80%, pI 3-10 20%) Glycerol (10%) for 1 hour. Separation was performed as per manufacturers recommendation (Pharmacia Biotechnology, Dry IEF instruction bulletin) and stained with coomassie R-250. The sample migrated as a single protein band with an isoelectric point of about 2.8.

Western Blots of the HPSEC FAE sample were performed using PVDF membranes (0.2 µm pore size) a Novex mini-gel apparatus for obtaining N-terminal amino acid sequence by methods recommended by manufacturer. A sample of the FAE in dialysed into buffer (5 mM MES pH 5.8).

The resultant purified protein was placed in an aqueous solution for peptide sequence analysis according to standard methods. Briefly the peptides were digested in solution with the following sequencing grade proteases:

Lys-C—200 µl reaction buffer comprising 100 mM ammonium bicarbonate and 2–4 µg of enzyme, pH 8.0, overnight at 37° C.;

Arg-C—200 µl reaction buffer comprising 20 mM Tris and 4 µg of enzyme, pH 7.5+1.5 mM $CaCl_2$+2 mM DTT overnight at 37° C.;

Glu-C—digest buffer for on-blot digests was 50 mM ammonium bicarbonate with 4 µg enzyme, 10% acetonitrile and 1% reduced triton X-100;

CNBr cleavage—was conducted by dissolving enzyme sample in 200 µl of 70% formic acid in water and CNBr crystals added in sufficient quantity to produce methionine cleavage.

The digested peptides were then concentrated to approximately 100 µl and loaded is directly onto a reverse-phase HPLC (Phenomenex Primesphere C18 column, 250×2.0 mm). Reverse phase separations were carried out using Applied Biosystems 140A solvent delivery system. Buffers used were 0.1% TFA in water (A), 70% acetonitrile in water+0.070% TFA (B); flow rate was 150 µl per minute with a gradient as follows: 0 minutes—5% Buffer B, 10 minutes—10% Buffer B, 80 minutes—80% Buffer B, 85 minutes—100% Buffer B, 90 minutes—100% Buffer B.

CNBr digests are treated as follows: water is added to the solution and the whole volume concentrated to 100 µl in a speed-vac. Further water is added to approximately 1 ml and this dried again to about 100 µl. This removes the majority of the formic/CNBr.

Various peptide fragments obtained as described above were analyzed to determine their sequence and for subsequent development of degenerate probes for use in cloning the gene encoding the 38 kD esterase from the genome of the donor organism. Peptide sequence analysis of the 38 kD esterase was problematic due to cycles containing mixed signals indicating the presence of multiple polypeptides in the analyzed sample. Protein sequencing resulted in an N-terminal sequence and several additional peptide fragments as follows:

| | |
|---|---|
| ASTQGISEDLYSRLVEMATISQAAYXDLLNIP | (SEQ. ID NO:1) |
| XTVGFGPY | (SEQ. ID NO:2) |
| FGLHLXQXM | (SEQ. ID NO:3) |
| XISEDLYS | (SEQ. ID NO:4) |
| YIGWSFYNA | (SEQ. ID NO:5) |
| GISEDLYXXQ | (SEQ. ID NO:6) |
| XISESLYXXR | (SEQ. ID NO:7) |
| GISEDLY | (SEQ. ID NO:8) |
| LEPPYTG | (SEQ. ID NO:9) |
| XANDGIPNLPPVEQ | (SEQ. ID NO:10) |
| YPDYALYK | (SEQ. ID NO:11) |

From these fragments, suitable degenerate probes for hybridization and use as PCR primers were produced and fragments were obtained which were believed to be derived from the gene encoding the 38 kD esterase. However, sequencing of the fragments obtained in this manner (550 and 100 base pairs) showed that the fragments were merely artifacts of PCR and were not of use in cloning the 38 kD esterase. Additional analysis of 2 different probes derived from 2 protein sequences isolated as above resulted in similar lack of success. From these results, it was determined that routine protein purification and peptide sequencing procedures were insufficient to obtain suitable peptide fragments for the preparation of degenerate DNA probes.

The inventors herein hypothesized that a specific property of the protein or the purified protein composition was preventing obtaining purified representative protein. To test this theory, the product protein from above was analyzed via isoelectric focusing gel at pH 2–4 under various conditions. Protein samples taken from purification steps along the purification method described above appeared to be a single band of highly purified protein. A second analysis was performed in which the purified protein was subjected to denaturing conditions of an SDS-PAGE and the results western blotted. As shown in FIG. 1, the resultant protein showed a number of bands indicating either some degeneration of the protein or other compounds hidden during the IEF gel. Sequencing of each of the numerous bands showed that each possessed an identical N-terminal sequence and that proteolysis appeared to be occurring from the carboxy terminal.

From the data, the inventors herein hypothesized that numerous fragments may be appearing due to carboxy terminal proteolytic clipping within the molecule itself upon unfolding of the protein in reduced SDS buffer. Unfolding of the 38 kD esterase may expose the previously internal hydrophobic residues, e.g., tyrosine, tryptophan and phenylalanine, providing a structurally similar substrate to the ester linked feruloyl group which would be recognized in the active site of the 38 kD esterase allowing for hydrolysis peptide. This result was highly unpredictable due to the fact that the heretofore observed enzymatic action of the isolated protein was esterolytic and not proteolytic. In any event, the inventors herein theorized that if protein denaturing conditions (i.e., unfolding of the peptide chain) were avoided, internal clipping may be avoided. To effect this, the purified protein from the anion exchange chromatography step was further chromatographed using high resolution size exclusion chromatography (HPSEC as detailed above).

The HPSEC purified 38 kD esterase was separated by SDS-PAGE and a Western blot onto a PVDF membrane was performed for sequencing "on-blot". Digests directly from the blots were prepared as follows: neat TFA is added to the blot containing solution to give a final volume containing 50% TFA. This solution is then sonicated for 5 minutes. The liquid (but not the blot pieces) is removed and a solution of 50% acetonitrile in 0.1% TFA is added. The sample is sonicated again for 5 minutes. The liquid was removed and replaced by a final wash of 0.1% TFA in water and a final 5 minutes sonication. All wash solutions were pooled and concentrated down to approximately 100 µl. This method allowed for the polypeptides resulting from enzymatic digests to be collected without further proteolysis by 38 kD esterase immobilized on the membrane. In this way, single polypeptides suitable for sequence analysis were obtained due to 38 kD esterase being immobilized on the PVDF thus preventing carboxy terminal proteolytic clipping and the presence of mixed amino acid signals during each cycle of sequencing.

When this procedure was followed, a number of fragments which were appropriate for the design of degenerate DNA fragments were produced.

Example 2

Isolation of A 650 Base Pair Fragment Corresponding to FAE Gene

Based on the peptide fragments obtained in Example 1 after the protein clipping problem had been solved, the gene encoding the 38 kD esterase was cloned by amplifying the gene from its genome using polymerase chain reaction and appropriately designed degenerate oligonucleotide primers. Primers were designed based upon partial amino acid sequences of fragmented 38 kD esterase protein. Amplification of three fragments from the 38 kD esterase gene was obtained using the following four oligonucleotide primers (the oligonucleotide primers were designed based upon the underlined peptide sequence following the oligonucleotide primers. The following abbreviations were used to identify wobble position alternates: I=inosine, W=A/T, S=C/G, R=A/G, Y=T/C, H=A/T/C, D=A/G/T, X=A/T/G/C.
Sense primer 11: CGGGAATTCGCIWSIACICARGGXAT (SEQ ID. NO:12)
Derived from: ASTQGISEDLYSRLVEMATISQAAYADLLNIP (SEQ ID. NO:13)
Sense primer 7: CGGGAATTCTAYTAYATHGGITGGGT (SEQ. ID NO:14)
Derived from: VHGG<u>YYIGWV</u>SVQDQV (SEQ. ID NO:15)
Anti-sense primer 8: CGGGAATTCACCCAICCDATRTARTA (SEQ. ID NO:16)
Derived from: VHGG<u>YYIGWV</u>SVQDQV (SEQ. ID NO:17)
Anti-sense primer 2: CGGGAATTCTTIGGIATICCRTCRTT (SEQ. ID NO:18)
Derived from: TDAFQASSPDTTQYFRVTH<u>ANDGIPNL</u> (SEQ. ID NO:19)

Two primers enabled deduction of putative amplified DNA fragments encoding the 38 kD esterase:
Anti-sense primer 3: CGGGAATTCATICCRTCRTTIGCRTG (SEQ. ID NO:20)
Derived from: TDAFQASSPDTTQYFRVT<u>HANDGIPNL</u> (SEQ. ID NO:21)
Anti-sense primer 12: CGGGAATTCGCYTGRAAIGCRTCIGTCAT (SEQ. ID NO:22)
Derived from: (M)TDAFQASSPDTTQYFRVTHANDGIPNL (SEQ. ID NO:23)

An EcoR I restriction endonuclease recognition site and a "GC" clamp was included at the 5' end of all primers to facilitate cloning of amplified fragments into the plasmid vector pUC18. PCR reaction included placing the following into "Hot Start" (Molecular Bio-Products, Inc., San Diego, Calif.) tubes in the order provided:
1 µl 500 ng/µl sense primer
1 µl 500 ng/µl anti-antisense primer
2 µl nucleotide mix (10 mM each dNTP)
5 µl 10× PCR Buffer
41 µl distilled water
  Heated at 95° C. for 90 seconds, placed onto ice for 5 minutes.
5 µl 10× PCR Buffer
43 µl distilled water
1 µl Aspergillus niger genomic DNA
1 µl Taq DNA Polymerase (Boehringer Mannheim, 5 U/µl)

Amplification was carried out in a Minicycler Model PTC -150 (MJ Research Inc., Watertown, Mass.). Amplification conditions followed a sequential pattern of: 95° C. for five minutes; 40° C. for 90 seconds; 72° C. for 3 minutes; and 28 cycles of 94° C. for 1 minute, 40° C. for 90 seconds, and 72° C. for 3 minutes for 28 cycles. A final extension step of 72° C. at 2 minutes was included.

The primers were used for PCR amplification in the following paired combinations: 11-2, 11-3, 11-8, 11-12, 7-2, 7-3 and 7-12. Each primer combination produce multiple DNA bands upon agarose electrophoresis. Major DNA bands for the PCR products of primers pairs 7-2, 7-3 and 7-12 were present at around 350, 350 and 300 base pairs respectively as visualized on a 3% NuSieve (FMC Corp.) agarose electrophoresis gel. Antisense primers 2, 3 and 12 were designed to the same continuous peptide fragment: (M)TDAFQASSPDTTQYFRVTHANDGIPNL (SEQ. ID NO: 24). Anti-sense primers 2 and 3 code for nearly the same stretch of DNA, their 3' ends being offset by only 6 bases. As antisense primer 12 corresponds to amino acids that are upstream of primers 2 and 3, the 3' end of antisense primer 12 is offset by approximately 60 base pairs from primers 2 and 3. Therefore, the lengths of the PCR bands were approximately consistent with a continuous stretch of DNA encoding the 38 kD esterase. Additionally the primer pairs 11-2, 11-3 and 11-12 produced bands of approximately 650, 650 and 600 base pairs respectively. These lengths were approximately consistent with amplification of a piece of DNA encoding the 38 kD esterase.

The PCR amplification products were digested with EcoRI, ligated into the cloning vector pUC18 and then transformed into E. coli. The cloned PCR products were sequenced. Sequencing of the product of primers 11-2 revealed a 650 base pair. DNA sequence shown in FIG. 2 (SEQ. ID NO:25) which upon translation codes for 197 amino acids. A total of 155 residues corresponded to nine sequenced peptide fragments of 38 kD esterase protein. A putative 57 base pair intron exists containing splicing sequences of GTATGC at the 5' site, an internal lariat sequence of CACTAACT, and TAG at the 3' splice site. Furthermore a product of primers 11-8 when sequenced reveals approximately the first 314 bases (5'-3') of the 650 base pair 11-2 fragment. A 350 base pair product of primers 7-2 revealed DNA that corresponds in sequence to the second half of the 650 base pair 11-2 fragment.

Example 3

Obtaining Genomic DNA from Aspergillus Niger for Cloning

A preserved culture of Aspergillus niger was grown on Potato Dextrose Agar (PDA) at 30° C. Approximately 2 cm$^2$ of the fungi grown on PDA was inoculated into 50 ml of Yeast Extract Glucose media in a 250 ml baffled flask and incubated at 33° C. in a rotary shaker at a speed of 300 RPM for 24 hours. The mycelia was harvested through miracloth, squeezed dry, immediately frozen in liquid nitrogen and ground with ½ teaspoon of sand in a mortar and pestle for approximately two minutes. The genomic DNA was extracted from the ground mycelia using a modification of Invitrogen's Easy-DNA Genomic Isolation Kit. The ground, frozen mycelia was immediately transferred to a centrifuge tube to which 3.5 mls of Solution A was added, followed by vortexing and a 10 minute incubation at 65° C. Next, 1.5 mls of Solution B was added, followed by vortexing. 5 mls of chloroform was added, followed by vortexing until the viscosity decreased and the mixture was homogeneous. The mixture was centrifuged at 15,000×G at 4° C. for 20 minutes. The upper phase was transferred into a new tube and then precipitated with two volumes of 95% ethanol. The precipitation reaction was incubated on ice for 30 minutes. The precipitation DNA was pelleted by centrifugation at 15,000×G at 4° C. for 15 minutes. The ethanol was removed. The DNA pellet was washed with 25 mls of 70% ethanol and the mixture was centrifuged at 15,000×G at 40° C. for 5 minutes. The 70% ethanol was removed and the pellet allowed to air dry for 5 minutes The extracted DNA was suspended in a volume of 500 µl of TE, RNase was added to a final concentration of 4 µg/ml. This extracted genomic DNA was used in PCR amplification of the DNA fragments encoding 38 kD esterase.

Example 4

Using the Obtained 650 Base Pair Fragment to Isolate DNA Encoding Homologous Enzymes from Aspergillus or Other Species One particularly effective method of obtaining clones of homologous genomic DNA is by construction and screening of a subgenomic libraries. Briefly, and as described in more detail below, this method involves cutting the genomic DNA to completion with appropriate restriction endonucleases, performing Southern hybridization with the 650 base pair fragment as a probe, ligating the appropriately sized fragments into a plasmid vector, transforming the plasmid into E. coli and then southern probing the colonies with the 650 base pair fragment to obtain a genomic clone. These techniques are known in the art and are described in Current Protocols in Molecular Biology, supra.

To obtain clones of a vector comprising the gene encoding the entire 38 kD esterase protein, Aspergillus niger genomic DNA was prepared as in Example 3. The genomic DNA was fragmented by digestion with a number of restriction enzymes: EcoR I, Hind III, PinA I, Mlu I, Spe I, Bgl II, Ppu10 I, Mfe I, Nco I, Bin I, Eag I and Xma I (supplied by New England Biolabs, Inc., Beverly, Mass. and Boehringer Mannheim). The reaction conditions combined 3 µl of genomic DNA, 2 µl of the appropriate 10× restriction endonuclease buffer (according to the manufacturers instructions), 2 µl of restriction enzyme (at 10 units/µl), 13 µl of distilled water; the reaction proceeded at 37° C. for 6 hours. The samples were then electrophoresed through a 0.7% agarose gel so that separation of DNA fragments could be visualized between a size of 1 kb to >12 kb. The gel was briefly rinsed in distilled H$_2$O and subsequently depurinated for 30 minutes in a solution of 0.25M HCl with gentle shaking followed by denaturation for 30 minutes in a solution of 0.4 M NaOH with gentle shaking. The DNA was then transferred onto a positively charged Maximum Strength Nytran Plus membrane (Schleicher & Schuell, Keene, N.H.) using a solution of 0.4 M NaOH as transfer solution. After the transfer was complete, >2 hours, the membrane was rinsed in 2×SSC and air dried. The membrane was then prehybridized for 8 hours in a prehybridization solution containing per 100 mls: 50 mls formamide, 25 mls of 20×SSPE (1×SSPE=0.18 M NaCl, 1 mM EDTA, 10 mM NaH$_2$PO$_4$, pH 7.7), 2.5 mls of 20% SDS, 1 ml of 10 mg/ml, sheared herring sperm DNA and 21.5 mls of distilled H$_2$O.

The cloned 650 base pair fragment of Example 2 was used as a hybridization probe of the membrane. The fragment was isolated from the pUC18 plasmid by restriction digestion with EcoR I, electrophoresis in 1% agarose, excision of the fragment from the gel and recovery of the fragment from the excised agarose. This purified 650 base pair fragment of DNA was random prime $^{32}$P labeled using the Megaprime labeling system according to the instructions of the manufacturer (Amersham International plc, Buckinghamshire, England). The labeled probe was denatured by heating to 100° C. for 5 minutes and immediately added to the prehybridization solution containing the membrane. The hybridization reaction proceeded for 18 hours at 37° C. with gentle shaking. The membrane was rinsed in a solution of 2×SSC/ 0.3% SDS and then washed for 15 minutes in the same solution at 37 ° C. with shaking. The membrane was further washed with a solution of 0.2×SSC/0. 1% SDS at 37° C. for 30 minutes. The membrane was then exposed onto X-Omat AR film (Eastman Kodak Co, Rochester, N.Y.) for 3 hours and developed.

The film developed from the digests prepared as above showed only one band of hybridization per restriction enzyme digestion consistent with hybridization. The EcoRI digestion showed a single band of hybridization at about 5.5 kb in length. Because this hybridized fragment was an excellent candidate fragment to contain a gene corresponding to the entire 38 kD esterase as a result of its size being consistent with a gene encoding a protein of that size, a sub-library was made choosing EcoR I to digest genomic Aspergillus niger DNA to obtain fragment sizes around 5.5 kb in length.

A restriction digest was made on genomic DNA prepared as in Example 3. The reaction included 50 µl of genomic DNA, 50 µl of 10× restriction endonuclease buffer H (Boehringer Mannheim), 25 µl of EcoRI (10 units/µl, Boehringer Mannheim), 375 µl of distilled water. The reaction proceeded at 37° C. for 6 hours. The digestion mixture was electrophoresed through 0.8% agarose. Fragments between a range of approximately 5 kb to 6 kb were cut from the gel in three approximately equal slices. The three pools of DNA fragments contained within the three gel slices each possessed a slightly different range of fragment lengths. The DNA was recovered from the slices of agarose using Q/Aquick Gel Extraction columns, following the instructions of the manufacturer (Qiagen, Inc., Chatsworth, Calif.). Approximately ¹/₁₀ of each pool of recovered DNA was electrophoresed in 0.8% agarose and southern hybridized to the 650 base pair fragment as described above. The pool of DNA which gave the strongest hybridization signal was ligated into an EcoR I digested E. coli vector (for example pLITMUS 28, New England Biolabs), which was then transformed into E. coli . The E. coli transformants were plated out on 5 plates at a concentration of approximately 500 colonies per plate (150 mm diameter plate). Colony lifts were performed on the plates using Maximum Strength Nytran Plus membranes. A southern hybridization was performed using the 650 base pair fragment. Four strong hybridization signals were obtained. Colonies putatively corresponding to the four strong hybridization signals were grown up and their plasmid DNA recovered. Restriction digests on the plasmid DNA were made using restriction enzymes that were chosen based on sites within the 650 base pair fragment. One plasmid restriction digest gave restriction fragments consistent with the known restriction sites within the 650 base pair fragment. Upon DNA sequencing, this clone was revealed to contain the 650 base pair sequence that was obtained through PCR described in example 2. Restriction mapping of this clone reveals the 650 base pair fragment to lie within the approximately 5.5 kb of cloned genomic DNA sequence. Based on this procedure, DNA encoding the entire gene of the 38 kD esterase was isolated corresponding to the sequence provided in FIG. 5 (SEQ. ID. NO:27) encoding a protein having the amino acid sequence of FIG. 5 (SEQ. ID. NO:28).

Modifications of this method which are known to effect similar results would also be effective in obtaining the suitable DNA or clones. Of course, this method is similarly suitable for the identification and cloning of homologous esterase enzymes from species other than *Aspergillus niger*. For example, as described above, a genomic library could be produced from a suitable microorganism by preparing genomic DNA and cutting with an appropriate restriction endonuclease. The library would then be subjected to Southern Blot hybridization with the 650 base pair fragment described in Example 2 as a probe and suitable hybridizing fragments ligated into a suitable expression vector and transformed into a suitable organism for expression. Suitable techniques for such processes are described in, for example, European Patent No. 215 594 (Genencor).

Example 5

Construction of an Expression System for FAE

Production of FAE was achieved by constructing an expression vector and transforming that vector into Aspergillus. The transformed Aspergillus strain is then grown in appropriate fermentation media. An FAE expression vector is described below. Transformation of Aspergillus is known in the art and is described for example in "Cloning, mapping and molecular analysis of the pyrG (orotidine-5'-phosphate decarboxylase) gene of *Aspergillus nidulans*", B. Oakley et al., Gene, 61 (1987) pp. 385–399.

An FAE expression vector can be constructed in available E. coli plasmids like pNEB193 (New England Biolabs, Beverly, Mass.). Three elements are required for the expression vector. In brief these elements are: The FAE gene with its downstream terminator sequence, the A. niger glucoamylase promoter and the A. nidulans pyrG gene which is used as a selectable marker for transformation. The pyrG gene may be PCR amplified from Aspergillus nidulans FGSC4 obtainable from the Fungal Genetics Stock Center, Department of Microbiology, University of Kansas Medical Center, Kansas City, Kans. 66160-7420 USA. The FAE gene sequence is given in FIG. 6. The A. niger glucoamylase promoter and the A. nidulans pyrG DNA sequences may be obtained from the GenBank sequence database. The A. nidulans pyrG sequence is disclosed in Oakley et al. The DNA sequence of the A. niger glucoamylase promoter is disclosed in "Regulation of the glaA gene of *Aspergillus niger*," Fowler et al., Current Genetics (1990) 18:537–545. The elements were arranged in the E. coli plasmid in such a way that the glucoamylase promoter drives the expression of the fae1 gene starting from the fae1 start methionine codon (from base 519 in the fae1 gene). This allows the strong glucoamylase promoter to drive expression of the FAE gene product.

Methods for constructing DNA sequences in E. coli plasmids are known in the art. An acceptable method for constructing an FAE expression vector in the vector pNEB193 follows:

(a) PCR is used to amplify the A. nidulans pyrG gene and insert this sequence into pNEB193. This could be accomplished with two primers and suitable conditions to obtain a pyrG fragment of approximately 2.0 kb in size. For example, the upper primer may be:

5'-GGCCTGCAGCCCCGCAAACTACGGGTACGTCC-3' (SEQ.ID.NO:30)

and the lower primer may be:

5'-CGCGCTGCAGGCTCTTTCTGGTAATACTATGCTGG-3' (SEQ.ID.NO:31)

Aspergillus nidulans genomic DNA may be prepared for amplification as described above. The conditions needed to amplify a 2.0 kb fragment are known in the art, for example they are given in the "Expand High Fidelity PCR System" (Boehringer Mannheim, Indianapolis, Ind.). After amplification of the fragment, it is isolated and then digested with the enzyme Pst I. Also the plasmid pNEB193 is digested with Pst I. After digestion, the fragment and plasmid are isolated and ligated together.

(b) PCR is used to amplify the A. niger glucoamylase promoter and place this sequence into the plasmid constructed. This could be accomplished using two primers and conditions to obtain a promoter fragment of approximately 1.9 kb in size. As examples of suitable primer, the upper primer could be

5'-GGCTTAATTAACGTGCTGGTCTCGGATCTTTGGCGG-3' (SEQ.ID.NO:32)

and the lower primer could be:

5'-GGGGCGCGCCAGATCTAGTACCGATGTTGAGGATGAAGCTC-3' (SEQ.ID.NO:33).

While many different strains are suitable for amplification, one particularly useful strain for amplification is A. niger strain ATCC10864 (American Type Culture Collection, Rockville, Md.). The A. niger genomic DNA for amplification may be isolated as described above. After amplification the fragment is isolated and digested with the enzymes Pac II and Asc I. The plasmid created in (a) above above is also be digested with the enzymes Pac II and Asc I. The digests of both the amplified fragment and plasmid would be ligated together.

(c) Two fragments of the FAE gene are combined into the plasmid created in (b) utilizing the a 5.5 kb EcoRI fragment comprising the entire FAE gene. The first fragment is created via PCR using the following primers in connection with the 5.5 kb EcoRI fragment of the FAE gene disclosed above as the source to be amplified:

forward primer: 5'-GCCCAGATCTCCGCAATG AAGCAATTCTCCGCCAAACAC-3' (SEQ.ID.NO:34)

reverse primer: 5'-AATAGTCGACGGAAT GTTGCACAGG-3' (SEQ.ID.NO:35)

This fragment is digested with Bgl II and Sal I to result in a fragment of about 169 base pairs long. The second fragment is made by incubating the 5.5 kb EcoRI fragment of the FAE gene with SalI and EcoRI, the resulting 1.75 kb fragment being isolated. The plasmid created in (b) above is prepared for insertion of the FAE gene by digesting with Bgl II and EcoRI. The three fragments, the 169 base pair PCR product, the 1.75 kb fragment and the Bgl II/EcoRI digested step 2 plasmid, are ligated together. This resulting plasmid would be an Aspergillus FAE gene expression vector.

The vector created above would be used to carry out transformation of Aspergillus.

Example 6

Identification of Homologous Genes in Filamentous Fungi

A southern hybridization experiment was performed under hybridization conditions described using 25% formamide in hybridization buffer as defined herein. The 650 base pair FAE gene fragment isolated in Example 2 was used to probe digested genomic DNA from a number of genera. Hybridization bands were obtained with genomic DNA obtained from fungi other than *Aspergillus niger* implying the existence of homologous esterase genes in these other organisms. Based on the hybridization data, it is believed that the DNA identified in this experiment will code for closely related enzymes with esterolytic activity. The genes for these other homologous enzymes are cloned by the methods described. These cloned genes are then expressed in suitable hosts to produce the encoded enzyme.

The genomic DNA was digested with two restriction enzymes, Bgl II and Ppu10 I, and then electrophoresed through 0.7% agarose in two different gels. Genomic DNA fragment sizes separated on the agarose gel ranged from about 1 kb to about 20 kb. The gels were depurinated and denatured and Southern blotted onto Nytran plus. The membranes were air dred and hybridized with the 650 base pair fragment $^{32}$P labeled. The membranes were washed under low stringency conditions, followed by washing under standard stringency conditions. The membranes were then autoradiographed. The reproduced gels are provided in FIGS. 6 and 7.

| lane # | endonuclease | DNA source |
| --- | --- | --- |
| gel 1 | | |
| 2 | Bgl II digest | *Aspergillus niger* GCI strain #7 |
| 3 | Ppu10 I digest | *Aspergillus niger* GCI strain #7 |
| 4 | Bgl II digest | *Aspergillus terrus* |
| 5 | Ppu10 I digest | *Aspergillus terrus* |
| 6 | Bgl II digest | *Trichoderma reesei* strain QM6a, ATCC13631 |
| 7 | Ppu10 I digest | *Trichoderma reesei* strain QM6a, ATCC13631 |
| 8 | Bgl II digest | *Acremonium brachypenium*, ATCC 32206 |
| 9 | Ppu10 I digest | *Acremonium brachypenium*, ATCC 32206 |
| gel 2 | | |
| 17 | Bgl II digest | *Aspergillus niger* GCI strain #7 |
| 18 | Ppu10 I digest | *Aspergillus niger* GCI strain #7 |
| 19 | Bgl II digest | *Gliocladium roseum* |
| 20 | Ppu10 I digest | *Gliocladium roseum* |

-continued

| lane # | endonuclease | DNA source |
| --- | --- | --- |
| 25 | Bgl II digest | *Penicillium notatum* |
| 26 | Ppu10 I digest | *Penicillium notatum* |

Bands are apparent in lanes 2, 3, 17 and 18 which correspond to the cloned FAE gene described in this patent. Bands appear in the lanes 2 and 17 Bgl II digest which may indicate other homologous FAE enzymes present in the *Aspergillus niger* strain. Two bands are present in lanes 4 and 5 and two bands are present in lane 4, indicating homologous DNA in the *Aspergillus terrus*. A band is apparent in lane 7 indicating homologous DNA in *Trichodermna reesei*. A band is apparent in lane 8 indicating homologous DNA in *Acremonium brachypenium*. A band is apparent in lane 19 indicating homologous *Gliocladium roseum*. Two bands are present in lanes 25 and 26 indicating homologous DNA in *Penicillium notatum*.

Example 7

Biochemical Properties and Substrate Specificity of FAE Purified According to Example 1

The 38 kD esterase isolated according to Example 1 was analyzed for biochemical properties. The molecular weight was found to be about 38 kD when measured on SDS-PAGE and 30–32 kD as measured by HPSEL. The pl as measured on isoelectric focusing (IEF) gel was found to be about 2.8. Purified 38 kD esterase was found to be active toward several natural feruloyl and p-coumaroyl esters, cell walls of wheat bran and sugar beet pulp, wheat flour, the pentosan fraction of wheat flour, and ethyl and methyl esters of ferulic and p-coumaric acid. Kinetic data for various substrates is presented in Table 1. The 38 kD esterase showed a pH optimum of 5.1 for methyl ferulate with 83% and 25% maximal activity found at pH 3 and 8, respectively. When the 38 kD esterase was incubated in buffer for 30 minutes without substrate at pH 5.1, the temperature optima was 55° C. With 250 $\mu$M methyl ferulate present the optima increases to 65° C. A low $K_m$ of the trisaccharide FAXX favors the use of the 38 kD esterase of the present invention in combination with a xylanase that leaves such carbohydrate oligomers preferentially unhydrolyzed when degrading cell walls.

Purified 38 kD esterase was analyzed for a variety of biochemical activities with an API-20 enzyme test strip (BioMerieux Vitek) according to the manufacturers instructions. The results shown in Table 2. Activity was observed on the following substrates. "+++" indicates very strong response, "++" indicates strong response and "+" indicates activity shown towards substrate. "–" means no activity detected.

TABLE 1

Activity of 38kD Esterase On Various Feruloylated Oligosaccharides

| Substrate | $K_m$ (mM) | $V_{max}$ (U/mg) | $V_{max}/K_m$ |
| --- | --- | --- | --- |
| Methyl-FA | 2.08 | 87 | 41.8 |
| FA | 0.125 | 245 | 1960.0 |
| FAX | 0.078 | 276 | 3539.5 |
| FAXX | 0.019 | 498 | 26210.5 |
| FAX$_3$ | 0.052 | 307 | 5903.8 |

TABLE 2

Substrate Specificity For 38 kD Esterase

| Substrate | Activity | Enzyme Generally Associated With Activity |
|---|---|---|
| 2-naphthyl butyrate [pH 6.5] | (+++) | Esterase (C4) |
| 2-naphthyl caprylate [pH 7.5] | (++) | Esterase/Lipase (C8) |
| 2-naphthyl myristate [pH 7.5] | (+) | Lipase (C14) |
| 2-naphthyl phosphate [pH 5.4] | (+) | Acid Phosphotase |
| Naphthol-AS-BI-phosphate [pH 5.4] | (++) | Phosphohydrolase |
| 6-Br-2-naphthyl-αD-galactopyranoside [pH 5.4] | (+++) | α-galactosidase |
| 2-naphthyl-βD-galactopyranoside [pH 5.4] | (++) | β-galactosidase |
| 2-naphthyl-αD-glucopyranoside [pH 5.4] | (+) | α-glucosidase |
| 6-Br-2-naphthyl-βD-glucopyranoside [pH 5.4] | (+++) | β-glucosidase |
| 2-naphthyl phosphate [pH 8.5] | – | Alkaline Phosphotase |
| L-leucyl-2-naphthylamide [pH 7.5] | – | Leucine arylamidase |
| L-valyl-2-naphthylamide [pH 7.5] | – | Valine arylamidase |
| L-cystyl-2-naphthylamide [pH 7.5] | – | Cysteine Arylamidase |
| N-glutaryl-phenylalanine-2-naphthylamide | – | Chymotrypsin |
| N-benzoyl-DL-arginine-2-naphthylamide [pH 8.5] | – | Trypsin |
| Naphthol-AS-BI-βD-glucuronide [pH 5.4] | – | β-Glucuronidase |
| 6-Br-2-naphthyl-αD-mannopyronoside [pH 5.4] | – | α-Mannosidase |
| 2-naphthyl-αL-fucopyranoside [pH 5.4] | – | α-Fucosidase |

Example 8

Activity of the 38 kD Esterase Towards Sugar Beet Pulp Substrate

Sugar beet pulp (100 mg SBP) was incubated together with FAE (1.5 FAXX Units as measured by the method described in McCallum et al., *Analytical Biochemistry*, vol. 196, p. 362 (1991)) alone and in combination of 50 Units xylanase from *Trichoderma longibrachiatum* (Irgazyme 4x, available commercially from Genencor International, Inc.) in sodium acetate buffer (100 mM, pH 5.0). The reaction mixtures were continuously inverted at 25° C. during incubation. SBP incubated with (i) buffer alone, (ii) xylanase alone, or (iii) boiled FAE served as controls. Reactions were halted at 12 and 24 hours by the addition of 1.1 equivalents of HCL. Determination of total ferulic acid content of SBP was determined by saponification with NaOH by the method of Bomeman et al., *Appl. Microbiol. Biotech.* vol. 33, pp. 345–351 (1990). Ferulic acid released by enzymatic treatment was determined by HPLC using authentic ferulic acid standards (Aldrich) by the method of Bomeman et al., *Anal. Biochem.*, vol. 190, pp.129–133 (1990). Results are shown in table 3.

TABLE 3

Release of ferulic acid from sugar beet pulp with ferulic acid esterase
Ferulic acid released from sugar beet pulp

| Enzyme treatment | 12 hrs | | 24 hrs | |
|---|---|---|---|---|
| | μg | % | μg | % |
| FAE | 15.3 | 2.7 | 26.2 | 4.6 |
| Xylanase | 0.5 | 0.1 | 0.6 | 0.1 |
| FAE + Xylanase | 27.1 | 4.8 | 49.7 | 8.7 |
| Buffer Control | 0.2 | 0.04 | 0.2 | 0.04 |
| Inactivated FAE | 0.2 | 0.03 | 0.2 | 0.04 |

Of course, it should be understood that a wide range of changes and modifications can be made to the preferred embodiment described above. It is therefore intended that the foregoing detailed description be understood in the context of the following claims, including all equivalents, which are intended to define the scope of this invention.

---

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 32 amino acids
      (B) TYPE: amino acid
      (C) STRANDEDNESS: single
      (D) TOPOLOGY: linear (xi) SEQUENCE DESCRIPTION: SEQ ID NO:1:

Ala Ser Thr Gln Gly Ile Ser Glu Asp Leu Tyr Ser Arg Leu Val Glu
1             5              10            15

```
Met Ala Thr Ile Ser Gln Ala Ala Tyr Xaa Asp Leu Leu Asn Ile Pro
         20                  25                  30
```

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:2:

```
Xaa Thr Val Gly Phe Gly Pro Tyr
 1               5
```

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:3:

```
Phe Gly Leu His Leu Xaa Gln Xaa Met
 1               5
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:4:

```
Xaa Ile Ser Glu Asp Leu Tyr Ser
 1               5
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:5:

```
Tyr Ile Gly Trp Ser Phe Tyr Asn Ala
 1               5
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:6:

```
Gly Ile Ser Glu Asp Leu Tyr Xaa Xaa Gln
 1               5                  10
```

(2) INFORMATION FOR SEQ ID NO:7:

(i) SEQUENCE CHARACTERISTICS:
        (A) LENGTH: 10 amino acids

```
            (B) TYPE: amino acid
            (C) STRANDEDNESS: single
            (D) TOPOLOGY: linear (xi) SEQUENCE DESCRIPTION: SEQ ID NO:7:

Xaa Ile Ser Glu Ser Leu Tyr Xaa Xaa Arg
1               5                   10

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:8:

Gly Ile Ser Glu Asp Leu Tyr
1               5

(2) INFORMATION FOR SEQ ID NO:9:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:9:

Leu Glu Pro Pro Tyr Thr Gly
1               5

(2) INFORMATION FOR SEQ ID NO:10:

(i) SEQUENCE CHARACTERISTICS:
            (A) LENGTH: 14 amino acids
            (B) TYPE: amino acid
            (C) STRANDEDNESS: single
            (D) TOPOLOGY: linear (xi) SEQUENCE DESCRIPTION: SEQ ID NO:10:

Xaa Ala Asn Asp Gly Ile Pro Asn Leu Pro Pro Val Glu Gln
1               5                   10

(2) INFORMATION FOR SEQ ID NO:11:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:11:

Tyr Pro Asp Tyr Ala Leu Tyr Lys
1               5

(2) INFORMATION FOR SEQ ID NO:12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:12:

CGGGAATTCG CWSACCARGG AT                                    22
```

(2) INFORMATION FOR SEQ ID NO:13:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:13:

```
Ala Ser Thr Gln Gly Ile Ser Glu Asp Leu Tyr Ser Arg Leu Val Glu
 1               5                  10                  15
Met Ala Thr Ile Ser Gln Ala Ala Tyr Ala Asp Leu Leu Asn Ile Pro
            20                  25                  30
```

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:14:

CGGGAATTCT AYTAYATHGG TGGGT                        25

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:15:

```
Val His Gly Gly Tyr Tyr Ile Gly Trp Val Ser Val Gln Asp Gln Val
 1               5                  10                  15
```

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

CGGGAATTCA CCCACCDATR TARTA                        25

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:17:

```
Val His Gly Gly Tyr Tyr Ile Gly Trp Val Ser Val Gln Asp Gln Val
 1               5                  10                  15
```

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:18:

CGGGAATTCT TGGATCCRTC RTT                                                        23

(2) INFORMATION FOR SEQ ID NO:19:

(i) SEQUENCE CHARACTERISTICS:
            (A) LENGTH: 27 amino acids
            (B) TYPE: amino acid
            (C) STRANDEDNESS: single
            (D) TOPOLOGY: linear (xi) SEQUENCE DESCRIPTION: SEQ ID NO:19:

Thr Asp Ala Phe Gln Ala Ser Ser Pro Asp Thr Thr Gln Tyr Phe Arg
 1               5                  10                  15

Val Thr His Ala Asn Asp Gly Ile Pro Asn Leu
            20                  25

(2) INFORMATION FOR SEQ ID NO:20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:20:

CGGGAATTCA TCCRTCRTTG CRTG                                                       24

(2) INFORMATION FOR SEQ ID NO:21:

(i) SEQUENCE CHARACTERISTICS:
            (A) LENGTH: 27 amino acids
            (B) TYPE: amino acid
            (C) STRANDEDNESS: single
            (D) TOPOLOGY: linear (xi) SEQUENCE DESCRIPTION: SEQ ID NO:21:

Thr Asp Ala Phe Gln Ala Ser Ser Pro Asp Thr Thr Gln Tyr Phe Arg
 1               5                  10                  15

Val Thr His Ala Asn Asp Gly Ile Pro Asn Leu
            20                  25

(2) INFORMATION FOR SEQ ID NO:22:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:22:

CGGGAATTCG CYTGRAAGCR TCGTCAT                                                    27

(2) INFORMATION FOR SEQ ID NO:23:

(i) SEQUENCE CHARACTERISTICS:
            (A) LENGTH: 28 amino acids
            (B) TYPE: amino acid
            (C) STRANDEDNESS: single
            (D) TOPOLOGY: linear (xi) SEQUENCE DESCRIPTION: SEQ ID NO:23:

Met Thr Asp Ala Phe Gln Ala Ser Ser Pro Asp Thr Thr Gln Tyr Phe
 1               5                  10                  15

Arg Val Thr His Ala Asn Asp Gly Ile Pro Asn Leu (2) INFORMATION FOR SEQ ID NO:24:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:24:

```
Met Thr Asp Ala Phe Gln Ala Ser Ser Pro Asp Thr Thr Gln Tyr Phe
1               5                   10                  15

Arg Val Thr His Ala Asn Asp Gly Ile Pro Asn Leu
            20                  25
```

(2) INFORMATION FOR SEQ ID NO:25:

(i) SEQUENCE CHARACTERISTICS:
        (A) LENGTH: 650 base pairs
        (B) TYPE: nucleic acid
        (C) STRANDEDNESS: single
        (D) TOPOLOGY: linear (xi) SEQUENCE DESCRIPTION: SEQ ID NO:25:

```
GCCTCTACGC AGGGCATCTC CGAAGACCTC TACAGCCGTT TAGTCGAAAT GGCCACTATC      60
TCCCAAGCTG CCTACGCCGA CCTGTGCAAC ATTCCGTCGA CTATTATCAA GGGAGAGAAA     120
ATTTACAATT CTCAAACTGA CATTAACGGA TGGATCCTCC GCGACGACAG CAGCAAAGAA     180
ATAATCACCG TCTTCCGTGG CACTGGTAGT GATACGAATC TACAACTCGA TACTAACTAC     240
ACCCTCACGC CTTTCGACAC CCTACCACAA TGCAACGGTT GTGAAGTACA CGGTGGATAT     300
TATATTGGAT GGGTCTCCGT CCAGGACCAA GTCGAGTCGC TTGTCAAACA GCAGGTTAGC     360
CAGTATCCGG ACTATGCGCT GACTGTGACG GGCCACAGGT ATGCCCTCGT GATTTCTTTC     420
AATTAAGTGT ATAATACTCA CTAACTCTAC GATAGTCTCG GAGCGTCCCT GGCAGCACTC     480
ACTGCCGCCC AGCTGTCTGC GACATACGAC AACATCCGCC TGTACACCTT CGGCGAACCG     540
CGCAGCGGCA ATCAGGCCTT CGCGTCGTAC ATGAACGATG CCTTCCAAGC CTCGAGCCCA     600
GATACGACGC AGTATTTCCG GGTCACTCAT GCCAACGACG GCATCCCAAA                650
```

(2) INFORMATION FOR SEQ ID NO:26:

(i) SEQUENCE CHARACTERISTICS:
        (A) LENGTH: 197 amino acids
        (B) TYPE: amino acid
        (C) STRANDEDNESS: single
        (D) TOPOLOGY: linear (xi) SEQUENCE DESCRIPTION: SEQ ID NO:26:

```
Ala Ser Thr Gln Gly Ile Ser Glu Asp Leu Tyr Ser Arg Leu Val Glu
1               5                   10                  15

Met Ala Thr Ile Ser Gln Ala Ala Tyr Ala Asp Leu Cys Asn Ile Pro
                20                  25                  30

Ser Thr Ile Ile Lys Gly Glu Lys Ile Tyr Asn Ser Gln Thr Asp Ile
            35                  40                  45

Asn Gly Trp Ile Leu Arg Asp Asp Ser Ser Lys Glu Ile Ile Thr Val
        50                  55                  60

Phe Arg Gly Thr Gly Ser Asp Thr Asn Leu Gln Leu Asp Thr Asn Tyr
65                  70                  75                  80

Thr Leu Thr Pro Phe Asp Thr Leu Pro Gln Cys Asn Gly Cys Glu Val
```

```
                     85                  90                      95
His Gly Gly Tyr Tyr Ile Gly Trp Val Ser Val Gln Asp Gln Val Glu
               100                 105                 110
Ser Leu Val Lys Gln Gln Val Ser Gln Tyr Pro Asp Tyr Ala Leu Thr
           115                 120                 125
Val Thr Gly His Ser Leu Gly Ala Ser Leu Ala Ala Leu Thr Ala Ala
       130                 135                 140
Gln Leu Ser Ala Thr Tyr Asp Asn Ile Arg Leu Tyr Thr Phe Gly Glu
145                 150                 155                 160
Pro Arg Ser Gly Asn Gln Ala Phe Ala Ser Tyr Met Asn Asp Ala Phe
                165                 170                 175
Gln Ala Ser Ser Pro Asp Thr Thr Gln Tyr Phe Arg Val Thr His Ala
            180                 185                 190
Asn Asp Gly Ile Pro
        195

(2) INFORMATION FOR SEQ ID NO:27:

(i) SEQUENCE CHARACTERISTICS:
        (A) LENGTH: 2436 base pairs
        (B) TYPE: nucleic acid
        (C) STRANDEDNESS: single
        (D) TOPOLOGY: linear (xi) SEQUENCE DESCRIPTION: SEQ ID NO:27:

CCATGGTGGT GTCGATATCG GCAGTAGTCT TTGCCGAAAC GTTGAGGGTT ACAGTGATCT    60

GCGTCGGACA TACTTCGGGG AATCTACGGC GGAATATCAA AGTCTTCGGA ATATCCATAT   120

TGGGAAAGGA CAGAAGCTCC GGGGTAGTTT GATAGATGAG CTCCGGTGTA TTAAATCGGG   180

AGCTGACAGG AGTGAGCGTC ATGTAGACCA TCTAGTAATG TCAGTCGCGC GCAATTTCGC   240

ACATGAAACA AGTTGATTTC GGGACCCCAT TGTTACATCT CTCGGCTACA GCTCGAGATG   300

TGCCTGCCGA GTATACTTAG AAGCCATGCC AGCGTGTTGT TATACGACCA AAAGTCAGGG   360

AATATGAAAC GATCGTCGGA TATTTCTTGT TTTTATCCTA AATTAGTCTT CCAGTGGTTT   420

ATTTAAGAGA TAGATCCCTT CACAAACACT CATCCAACGG ACTTCTCATA CCACTCATTG   480

ACATAATTTC AAACAGCTCC AGGCGCATTT AGTTCAACAT GAAGCAATTC TCCGCCAAAC   540

ACGTCCTCGC AGTTGTGGTG ACTGCAGGGC ACGCCTTAGC AGCCTCTACG CAAGGCATCT   600

CCGAAGACCT CTACAGCCGT TTAGTCGAAA TGGCCACTAT CTCCCAAGCT GCCTACGCCG   660

ACCTGTGCAA CATTCCGTCG ACTATTATCA AGGGAGAGAA AATTTACAAT TCTCAAACTG   720

ACATTAACGG ATGGATCCTC CGCGACGACA GCAGCAAAGA AATAATCACC GTCTTCCGTG   780

GCACTGGTAG TGATACGAAT CTACAACTCG ATACTAACTA CACCCTCACG CCTTTCGACA   840

CCCTACCACA ATGCAACGGT TGTGAAGTAC ACGGTGGATA TTATATTGGA TGGGTCTCCG   900

TCCAGGACCA AGTCGAGTCG CTTGTCAAAC AGCAGGTTAG CCAGTATCCG GACTATGCGC   960

TGACTGTGAC GGGCCACAGG TATGCCCTCG TGATTTCTTT CAATTAAGTG TATAATACTC  1020

ACTAACTCTA CGATAGTCTC GGAGCGTCCC TGGCAGCACT CACTGCCGCC CAGCTGTCTG  1080

CGACATACGA CAACATCCGC CTGTACACCT TCGGCGAACC GCGCAGCGGC AATCAGGCCT  1140

TCGCGTCGTA CATGAACGAT GCCTTCCAAG CCTCGAGCCC AGATACGACG CAGTATTTCC  1200

GGGTCACTCA TGCCAACGAC GGCATCCCAA ACCTGCCCCC GGTGGAGCAG GGTACGCCCC  1260

ATGGCGGTGT AGAGTACTGG AGCGTTGATC CTTACGCGCC CAGAACACA TTTGTCTGCA  1320

CTGGGGATGA AGTGCAGTGC TGTGAGGCCC AGGGCGGACA GGGTGTGAAT AATGCGCACA  1380
```

```
CGACTTATTT TGGGATGACG AGCGGAGCCT GTACATGGTG ATCAGTCATT TCAGCCTCCC    1440

CGAGTGTACC AGGAAAGATG GATGTCCTGG AGAGGGCATG CATGTACGTA TACCCGAAGC    1500

ACACTTTTTC GGTAAATCAG GACATGTAAT AAGTTCCTTC CATGAATAGA TATGGTTACC    1560

CTCACCATAA GCCTTGAGGT TGCCTTTCTC TTTTGATTGT GAATATATAT TTAAAGTAGA    1620

TGACAGATAT CTCTAAACAC CTTATCCGCT TAAACCCATC ATAGATTGTG TCACGTGATA    1680

GACCCCTTGA ATGATGAGCG AAATGTATCA GTCCCGTTTA AATCAAACCC TTTCAGCCTA    1740

GCACAGTCAG AATACACCAA CCCCATTCTA AGGTAGTACT AAATATGAAT ACAGCCTAAA    1800

TGCATCGCTA TATGATCCCA TAAAGAAGCA ACAACCTTTC AGATCTCGTT TTGCGCTGCG    1860

AAGAGCTAGC TCTACCATGG TCTCAATTAT GAGTGGAGCG TTTAGTCTCG TTTAAGCCTA    1920

GCTATCTTAT AAGGACAACA CATGTACATG GGCTTACTTG TAGAGAGGTA GGATCCCGGG    1980

CTTCTTCACA TCTCGAGGAG TTGTCTACAC GTCGCGTCCA TGTCATAAGC CGGTACTCGA    2040

CGTTGTCGTG ACCGTGACCC AGACCCTGT TGATAGCGTT GAGAAGGCCC TATATTTGAA    2100

TTTCCAATCT CAGCTTTACG AAGATATGCC CATGGTGGAG GGTTAGTAAA CCGATGATGA    2160

TCGTGTGCAG CATGAGATGA GACCGTGGCC AATCCTGTTC AAATGCCAAG ACCCGCCTCC    2220

TACCACATGT AAGGCATCCG TCGGCCGCAC GTTGAATTGT GCAAATGCCG AGATCATAAA    2280

AGCGGCCACA CTTCCACGTC GGTACTGGAT GGGTTGCGCG TGGCCATACT GTGTTTTCCA    2340

TTGCGTGGGT CGTTCGTGTT ACTGCGACGC AGATTCTGTA GGCAAGGCGC AGGGCTCTCT    2400

TCTGAGGTAG AAAACACCCC ATATTAATCT GAATTC                              2436

(2) INFORMATION FOR SEQ ID NO:28:

(i) SEQUENCE CHARACTERISTICS:
        (A) LENGTH: 281 amino acids
        (B) TYPE: amino acid
        (C) STRANDEDNESS: single
        (D) TOPOLOGY: linear (xi) SEQUENCE DESCRIPTION: SEQ ID NO:28:

Met Lys Gln Phe Ser Ala Lys His Val Leu Ala Val Val Thr Ala
1               5                   10                  15

Gly His Ala Leu Ala Ala Ser Thr Gln Gly Ile Ser Glu Asp Leu Tyr
            20                  25                  30

Ser Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ser Gln Thr Asp Ile Asn Gly Trp Ile Leu Arg Asp Asp Ser Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Gly Cys Glu Val His Gly Gly Tyr Tyr Ile Gly Trp Val Ser Val
        115                 120                 125

Gln Asp Gln Val Glu Ser Leu Val Lys Gln Gln Val Ser Gln Tyr Pro
    130                 135                 140

Asp Tyr Ala Leu Thr Val Thr Gly His Ser Leu Gly Ala Ser Leu Ala
145                 150                 155                 160

Ala Leu Thr Ala Ala Gln Leu Ser Ala Thr Tyr Asp Asn Ile Arg Leu
```

```
                        165                  170                  175
Tyr Thr Phe Gly Glu Pro Arg Ser Gly Asn Gln Ala Phe Ala Ser Tyr
                180                  185                  190

Met Asn Asp Ala Phe Gln Ala Ser Ser Pro Asp Thr Thr Gln Tyr Phe
        195                  200                  205

Arg Val Thr His Ala Asn Asp Gly Ile Pro Asn Leu Pro Pro Val Glu
    210                  215                  220

Gln Gly Tyr Ala His Gly Gly Val Glu Tyr Trp Ser Val Asp Pro Tyr
225                  230                  235                  240

Ser Ala Gln Asn Thr Phe Val Cys Thr Gly Asp Glu Val Gln Cys Cys
                245                  250                  255

Glu Ala Gln Gly Gly Gln Gly Val Asn Asn Ala His Thr Thr Tyr Phe
            260                  265                  270

Gly Met Thr Ser Gly Ala Cys Thr Trp
        275                  280
```

(2) INFORMATION FOR SEQ ID NO:29:

(i) SEQUENCE CHARACTERISTICS:
        (A) LENGTH: 2436 base pairs
        (B) TYPE: nucleic acid
        (C) STRANDEDNESS: single
        (D) TOPOLOGY: linear (xi) SEQUENCE DESCRIPTION: SEQ ID NO:29:

```
CCATGGTGGT GTCGATATCG GCAGTAGTCT TTGCCGAAAC GTTGAGGGTT ACAGTGATCT      60

GCGTCGGACA TACTTCGGGG AATCTACGGC GGAATATCAA AGTCTTCGGA ATATCCATAT     120

TGGGAAAGGA CAGAAGCTCC GGGGTAGTTT GATAGATGAG CTCCGGTGTA TTAAATCGGG     180

AGCTGACAGG AGTGAGCGTC ATGTAGACCA TCTAGTAATG TCAGTCGCGC GCAATTTCGC     240

ACATGAAACA AGTTGATTTC GGGACCCCAT TGTTACATCT CTCGGCTACA GCTCGAGATG     300

TGCCTGCCGA GTATACTTAG AAGCCATGCC AGCGTGTTGT TATACGACCA AAAGTCAGGG     360

AATATGAAAC GATCGTCGGA TATTTCTTGT TTTTATCCTA AATTAGTCTT CCAGTGGTTT     420

ATTTAAGAGA TAGATCCCTT CACAAACACT CATCCAACGG ACTTCTCATA CCACTCATTG     480

ACATAATTTC AAACAGCTCC AGGCGCATTT AGTTCAACAT GAAGCAATTC TCCGCCAAAC     540

ACGTCCTCGC AGTTGTGGTG ACTGCAGGGC ACGCCTTAGC AGCCTCTACG CAAGGCATCT     600

CCGAAGACCT CTACAGCCGT TTAGTCGAAA TGGCCACTAT CTCCCAAGCT GCCTACGCCG     660

ACCTGTGCAA CATTCCGTCG ACTATTATCA AGGGAGAGAA AATTTACAAT TCTCAAACTG     720

ACATTAACGG ATGGATCCTC CGCGACGACA GCAGCAAAGA AATAATCACC GTCTTCCGTG     780

GCACTGGTAG TGATACGAAT CTACAACTCG ATACTAACTA CACCCTCACG CCTTTCGACA     840

CCCTACCACA ATGCAACGGT TGTGAAGTAC ACGGTGGATA TTATATTGGA TGGGTCTCCG     900

TCCAGGACCA AGTCGAGTCG CTTGTCAAAC AGCAGGTTAG CCAGTATCCG GACTATGCGC     960

TGACTGTGAC GGGCCACAGG TATGCCCTCG TGATTTCTTT CAATTAAGTG TATAATACTC    1020

ACTAACTCTA CGATAGTCTC GGAGCGTCCC TGGCAGCACT CACTGCCGCC CAGCTGTCTG    1080

CGACATACGA CAACATCCGC CTGTACACCT TCGGCGAACC GCGCAGCGGC AATCAGGCCT    1140

TCGCGTCGTA CATGAACGAT GCCTTCCAAG CCTCGAGCCC AGATACGACG CAGTATTTCC    1200

GGGTCACTCA TGCCAACGAC GGCATCCCAA ACCTGCCCCC GGTGGAGCAG GGGTACGCCC    1260

ATGGCGGTGT AGAGTACTGG AGCGTTGATC CTTACAGCGC CCAGAACACA TTTGTCTGCA    1320

CTGGGGATGA AGTGCAGTGC TGTGAGGCCC AGGGCGGACA GGGTGTGAAT AATGCGCACA    1380
```

```
CGACTTATTT TGGGATGACG AGCGGAGCCT GTACATGGTG ATCAGTCATT TCAGCCTCCC    1440

CGAGTGTACC AGGAAAGATG GATGTCCTGG AGAGGGCATG CATGTACGTA TACCCGAAGC    1500

ACACTTTTTC GGTAAATCAG GACATGTAAT AAGTTCCTTC CATGAATAGA TATGGTTACC    1560

CTCACCATAA GCCTTGAGGT TGCCTTTCTC TTTTGATTGT GAATATATAT TTAAAGTAGA    1620

TGACAGATAT CTCTAAACAC CTTATCCGCT TAAACCCATC ATAGATTGTG TCACGTGATA    1680

GACCCCTTGA ATGATGAGCG AAATGTATCA GTCCCGTTTA AATCAAACCC TTTCAGCCTA    1740

GCACAGTCAG AATACACCAA CCCCATTCTA AGGTAGTACT AAATATGAAT ACAGCCTAAA    1800

TGCATCGCTA TATGATCCCA TAAAGAAGCA ACAACCTTTC AGATCTCGTT TTGCGCTGCG    1860

AAGAGCTAGC TCTACCATGG TCTCAATTAT GAGTGGAGCG TTTAGTCTCG TTTAAGCCTA    1920

GCTATCTTAT AAGGACAACA CATGTACATG GGCTTACTTG TAGAGAGGTA GGATCCCGGG    1980

CTTCTTCACA TCTCGAGGAG TTGTCTACAC GTCGCGTCCA TGTCATAAGC CGGTACTCGA    2040

CGTTGTCGTG ACCGTGACCC AGACCCCTGT TGATAGCGTT GAGAAGGCCC TATATTTGAA    2100

TTTCCAATCT CAGCTTTACG AAGATATGCC CATGGTGGAG GGTTAGTAAA CCGATGATGA    2160

TCGTGTGCAG CATGAGATGA GACCGTGGCC AATCCTGTTC AAATGCCAAG ACCCGCCTCC    2220

TACCACATGT AAGGCATCCG TCGGCCGCAC GTTGAATTGT GCAAATGCCG AGATCATAAA    2280

AGCGGCCACA CTTCCACGTC GGTACTGGAT GGGTTGCGCG TGGCCATACT GTGTTTTCCA    2340

TTGCGTGGGT CGTTCGTGTT ACTGCGACGC AGATTCTGTA GGCAAGGCGC AGGGCTCTCT    2400

TCTGAGGTAG AAAACACCCC ATATTAATCT GAATTC                              2436

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:30:

GGCCTGCAGC CCCGCAAACT ACGGGTACGT CC                                    32

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:31:

CGCGCTGCAG GCTCTTTCTG GTAATACTAT GCTGG                                 35

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:32:

GGCTTAATTA ACGTGCTGGT CTCGGATCTT TGGCGG                                36

(2) INFORMATION FOR SEQ ID NO:33:
```

-continued

```
    (i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:33:

GGGGCGCGCC AGATCTAGTA CCGATGTTGA GGATGAAGCT                              40

(2) INFORMATION FOR SEQ ID NO:34:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:34:

GCCCAGATCT CCGCAATGAA GCAATTCTCC GCCAAACAC                               39

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:35:

AATAGTCGAC GGAATGTTGC ACAGG                                              25

-- 27 --

GC362-2-PCT
```

We claim:

1. An isolated DNA encoding the amino acid according to SEQ ID NO:28.

2. An isolated DNA capable of hybridizing under standard-stringency conditions with a DNA comprising at least 400 nucleotides of the DNA sequence according to SEQ ID NO: 29 and wherein said isolated DNA encodes a protein having esterolytic activity which cleaves the ester linkages of phenolic esters.

3. An expression vector comprising the DNA according to claim 1.

4. A host cell transformed with the DNA according to claim 1.

5. A host cell transformed with the expression vector according to claim 3.

6. A DNA which encodes a protein having esterolytic activity which cleaves the ester linkage of phenolic esters having a nucleotide sequence of SEQ ID NO: 29 or a portion of the sequence of SEQ ID NO: 29 wherein said portion comprises at least 400 nucleotides.

7. A method of producing an esterase comprising the steps of: (a) transforming a suitable microbial host cell with an expression vector comprising the DNA according to claims 1 or 2; and (b) cultivating said transformed host cell under conditions suitable for said host cell to produce said esterase.

8. The method according to claim 7 further comprising, (c) separating said produced esterase from said host cells to obtain a purified esterase.

9. A method of isolating a DNA which encodes a protein having esterolytic activity which cleaves the ester linkages of phenolic esters comprising: (a) creating a library comprising fragments from a first DNA derived from a plant, animal, fungus, yeast or bacteria; (b) combining said library of said first DNA with a probe comprising a second DNA under low-stringency to effect hybridization between said fragments in said library of DNA and said probe wherein said probe comprises DNA corresponding to SEQ ID NO: 29 or a portion thereof comprising at least 100 nucleotides; and (c) separating the hybridized DNA fragments from the non-hybridized fragments.

10. The method according to claim 9, wherein said first DNA is derived from a filamentous fungus.

11. The method according to claim 9, wherein said first DNA is derived from Aspergillus.

12. The method according to claim 9, wherein said conditions suitable for hybridization comprise standard-stringency conditions.

13. The method according to claim 9, wherein said probe comprises DNA corresponding to a portion of SEQ. ID NO:29 comprising at least 400 nucleotides.

14. DNA isolated according to the method of claim 9.
15. DNA isolated according to the method of claim 11.
16. DNA isolated according to the method of claim 12.
17. DNA isolated according to the method of claim 13.

* * * * *